(12) United States Patent
Ziv et al.

(10) Patent No.: US 7,510,825 B2
(45) Date of Patent: Mar. 31, 2009

(54) KITS AND METHODS FOR DETECTION OF APOPTOTIC CELLS

(75) Inventors: Ilan Ziv, Kfar Saba (IL); Anat Shirvan, Herzelia (IL)

(73) Assignee: NST NeuroSurvival Technologies Ltd, Petach-Tikva (IL)

( * ) Notice: Subject to any disclaimer, the term of this patent is extended or adjusted under 35 U.S.C. 154(b) by 0 days.

(21) Appl. No.: 11/172,934

(22) Filed: Jul. 5, 2005

(65) Prior Publication Data

US 2005/0244812 A1    Nov. 3, 2005

Related U.S. Application Data

(63) Continuation-in-part of application No. 10/433,668, filed as application No. PCT/IB01/02282 on Dec. 3, 2001.

(30) Foreign Application Priority Data

| Dec. 6, 2000 | (IL) | ................................... | 140114 |
| Feb. 21, 2001 | (IL) | ................................... | 141571 |
| Aug. 30, 2001 | (IL) | ................................... | 145210 |

(51) Int. Cl.
*C12Q 1/00* (2006.01)

(52) U.S. Cl. .......................................................... 435/4

(58) Field of Classification Search .................. 514/1; 435/4

See application file for complete search history.

(56) References Cited

U.S. PATENT DOCUMENTS 5,399,501 A    3/1995    Pope et al.

FOREIGN PATENT DOCUMENTS

| EP | 451 824 A2 | 10/1991 |
| SU | 1686373 | 10/1991 |
| WO | WO 99/27921 | 10/1991 |

OTHER PUBLICATIONS

Olive et al., Characterization of the uptake and toxicity of a fluorescent thiol reagent (p. 349-353), Cytometry, 3, (5) 1982.*

Hammermeister et al., Characterization of dansylated glutathione disulfide, cysteine and cystine by narrow bore liquid chromatography/electrospray ionization mass spectrometry (p. 503-508), Rapid Communications in Mass Spectrometry, 14, 2000.*

Rice, G, et al., "Use of N-Σ- dansyl-L-lysine and flow cytometry to identify heat-killed mammalian cells" Int. J. Hyperthermia 1, pp. 185-191 (1985).

Rehse,K, et al., "Oligoamines with Fluorescent Properties, Part B: Fluorophores in the Molecular Periphery". Arch. Pharm. 327, pp. 399-404 1994.

Muczynski, K, et al., "Incorporation of Dansylated Phospholipids and Dehydroergosterol into Membranes Using a Phospholipid Exchange Protein" Biochemistry 22, pp. 6037-6048 (1983).

Sekiguchi, R, et al., "The use of Dansyl Lysine to assess heat damage and theromotolerance of normal tissues" I.J. Radiation Oncology Biol. Phys. 14, pp. 983-988 (1988).

Epps, D, et al., "Determination of Dissociation Constants of High Affinity (pM) Human Renin Inhibitos: Application to Analogues of Ditekiren" J. Med. Chem. 34, pp. 2107-2112 (1991).

Fratazzi, C, et al., "Programmed Cell Death of Mycobacterium avium Serovar 4- Infected Human Macrophages Prevents the Mycobacteria from Spreading and Induces Mycobacterial Growth Inhibition by Freshly Added, Uninfected Macrophages" Journal of Immunology 158, pp. 4320-4327 (1997).

Selir,N, et al., "Polyamine sulfonamides with NMDA antagonist properties are potent calmodulin antagonists and cytotoxic agents" The International Journal of Biochemistry & Cell Biology 30 pp. 393-406 (1998).

Rodgers,G, et al., "Formation of Factor Va by Atherosclerotic Rabbit Aorta Mediates Factor Xa -catalyzed Prothrombin Activation" Journal of Clinical Invest. 81, pp. 1911-1919 (1988).

Callaghan, R, et al., "A comparison of membrane properties and composition between cell lines selected and tranfected for multi-drug resistance" Br. J. Cancer 66, pp. 781-786 (1992).

Taylor Jr., F.B., et al., "DEGR-Factor Xa Blocks Disseminated Intravascular Coagulation Initiated by *Escherichia coli* Without Preventing Shock or Organ Damage."Blood 178, pp. 364-368 (1991).

Hirose, K, et al., "Activated Protein C Reduces the Ischemia/Reperfustion-Induced Spinal Cord Injury in Rats by Inhibiting Neutrophil Activation" Annals of Surgery 232, pp. 272-280 (2000).

Humphries, G, et al., "Cholesterol-Free Phospholipid Domains May by The Membrane Feature selected by N-Σ-Dansyl-L-Lysine and Merocyanine 540" Biochemical and Biophysical Research Communications 111, pp. 768-774 (1983).

Robson, C, et al., "Chemical Synthesis and Biological Properties of Novel Fluorescent Antifolates in Pgp and MRP Overexpressing Tumor Cell Lines" Biochemical Pharmacology 56, pp. 807-816 (1998).

Berlot, J.P., et al., "Preparation of a dansylated fibrate, a new fluorescent tool to study peroxisome proliferation. Effect on hepatic-derived cell lines" Biochimie 79, pp. 145-150 (1997).

Hayakawa, M, et al., "Effects on mono dansyl cadaverine on platelet aggregations, blood coagulates and erythrocyte deformabilities" Japanese Journal of Geriatrics. 22, pp. 144-150 (Mar. 2, 1985) XP01127498.

Stary, H, et al., "A Definition of Advanced Types of atherosclerotic Lesions and a Histological Classification of Atherosclerosis" Circulation 92, pp. 1355-1374 (1995).

(Continued)

*Primary Examiner*—Yvonne (Bonnie) Eyler
*Assistant Examiner*—Chukwuma O. Nwaonicha
(74) *Attorney, Agent, or Firm*—Pearl Cohen Zedek Latzer, LLP

(57) ABSTRACT

The present invention provides kits and in vitro, in vivo or ex vivo detection methods by using compounds that bind selectively to cells undergoing perturbations and alterations of the normal organization of their cell membranes, such as cells undergoing apoptosis, while binding to a lesser degree to normal cells.

14 Claims, 29 Drawing Sheets

OTHER PUBLICATIONS

Van den Eijnde, S, et al., "Phosphatidylserine plasma membrane asymmetry in vivo: a pancellular phenomenon which alters during apoptosis" Cell Death and Differentiation 4, pp. 311-316, (1997).

Sims, P, et al., "Unraveling the Mysteries of Phospholipid Scrambling" Thromb Haemost 86, pp. 266-275 (2001).

Pugsley, P, et al., "The Impact of Microemboli During Cardiopulmonary Bypass on Neuropsychological Functioning" Stroke 25, pp. 1393-1399 (1994).

Martin, J, et al., "Early Redistribution of Plasma Membrane Phosphatidylserine is a General Feature of Apoptosis Regardless of the Initiating Stimulus: Inhibition by Overexpression of Bcl-2 and Abl" J. Exp. Med. 182, pp. 1545-1556 (1995).

Mallat, Z, et al., "Colocalization of Cpp-32 with Apoptotic Cells in Human Atherosclerotic Plaques" Circulation 96, pp. 424-428 (1997).

Kockx, M, et al., "Apoptosis atherosclerosis: beneficial or detrimental?" Cardiovascular Research 45, pp. 736-746 (2000).

Bursch, W, et al., "Cell death by apoptosis and its protective role against disease" TiPS 13, pp. 245-251 (1992).

Bratton, D, et al., "Appearance of Phosphatidylserine on Apoptotic Cells Requires Calcium-mediated Nonspecific Flip-Flop and Is Enhanced by Loss of the Aminophospholipid Translocase" The Journal of Biological Chemistry 272, pp. 26159-26165 (Oct. 17, 1997).

Bombeli, T, et al., "Apoptotic Vascular Endothelial Cells Become Procoagulant" Blood 89, pp. 2429-2442 (1997).

Bevers, E, et al., "Lipid translocation across the plasma membrane of mammalian cells" Biochimica et Biophysica Acta 1439, pp. 317-330 (1999).

Olive, P.L., et al. "Characterization of the Uptake and Toxicity of a Fluorescent Thiol Reagent", *Cytometry*, vol. 3, No. 5, p. 349-353, (1982).

Lazarides, E., et al. "Fluorescent localization of membrane sites in glycerinated chicken skeletal muscle fibers and the relationship of these sites to the protein composition of the Z disc", *Biochemistry*, vol. 75, No. 8, p. 3683-3687, (Aug. 1978).

Hochstrate, P., et al. "On the evaluation of Photoreceptor Properties by Micro-Fluorimetric Measurements of Fluorochrome Diffusion", *Biophysic of Structure and Mechanism*, vol. 6, p. 125-138, (1980).

Hammermeister, D.E., et al. "Characterization of dansylated glutathione, glutathione disulfide, cysteine and cystine by narrow bore liquid chromatography/electrospray ionization mass spectrometry", *Rapid Communications in Mass Spectrometry*, vol. 14, p. 503-508, (2000).

Atchanassakis et al., Journal of Receptors and Signal Transduction Research, 1999, 19(1-4), 143-154.

Verga et al., Mechanism of Allergic Cross-Reactions I Multispecific Binding of Ligands to a Mouse Monoclonal Anti-DNA IgE Antibody, Molecular Immunology, 1991, 28(6), 641-654.

Monogrodsky et al., Inhibition of Pokeweed Mitogen-Induced B Cell Differentiation by Compunds Containing Primary Amine of Hydrazine Groups, Clinical and Experimental Immunology, 1985, 59(1), 69-76.

\* cited by examiner

Fig. 19A
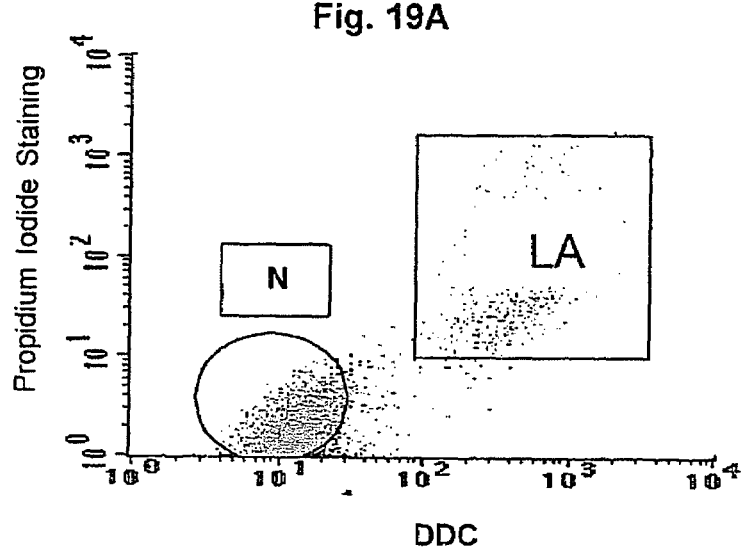
Fig. 19B
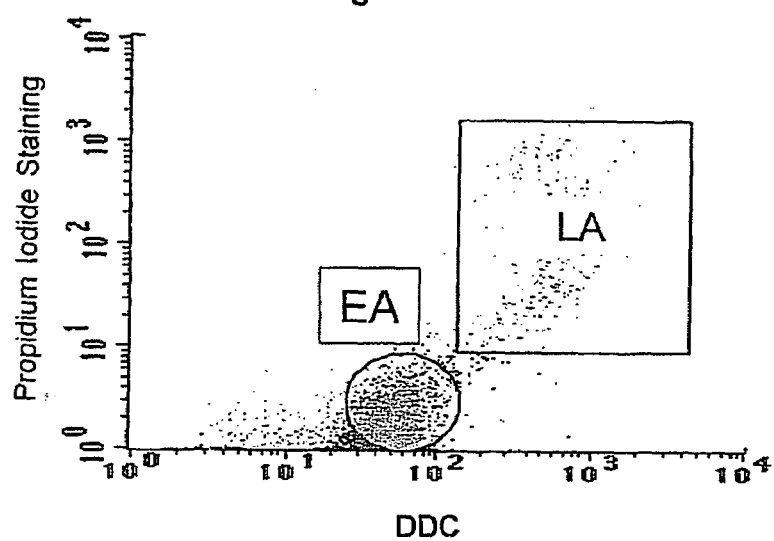
Fig. 19C
|  | Normal Cells | Early Apoptotic Cells | Late apoptotic Cells |
|---|---|---|---|
| Vivid™ Staining | - | + | + |
| Propidium Iodide Staining | - | - | + |

KITS AND METHODS FOR DETECTION OF APOPTOTIC CELLS

CROSS REFERENCE TO RELATED APPLICATIONS

This application is a Continuation in Part Application of U.S. application Ser. No. 10/433,668, filed Oct. 31, 2003, which is the National Phase Application of International PCT Application No. PCT/IB01/02282, International Filing Date Dec. 3, 2001, which claims priority of IL 140114, IL 141571 and IL 145210, filed Dec. 6, 2000, Feb. 21, 2001 and Aug. 30, 2001, respectively, which are incorporated hereto by reference by their entirety.

FIELD OF THE INVENTION

The invention relates to kits and diagnostic methods for detection of apoptotic cells in vitro, in vivo or ex vivo.

BACKGROUND OF THE INVENTION

The plasma membrane (outer membrane) of intact eukaryotic cells is characterized by a highly organized structure. This high level of membrane organization is determined, among others, by the molecular structure of the specific lipids constituting the membrane; the ratio between the various lipid species from which the membrane is composed; the distribution of the phospliolipids between the outer and inner leaflets of the membrane; and by the membrane protein constituents.

While maintenance of the high level of plasma membrane organization is fundamental to normal cell physiology, substantial perturbations and alterations of the normal organization of the cell plasma membrane (PNOM) occur in numerous physiological and pathological conditions, and are characterizing a plurality of diseases. Such alterations and perturbations may be evident both at the morphological level (membrane blebbing observed in cells undergoing apoptosis) and at the molecular level. PNOM includes, among others, scrambling and redistribution of the membrane phospholipids, with movement to the cell surface of aminophsopholipids, mainly phosphatidylserine (PS) and phosphatidylethanolamine (PE), which are normally restricted almost entirely to the inner leaflet of the membrane bilayer, and reciprocal movement of sphingomyelin (SM) and phosphatidylcholine (PC) from the outer leaflet to the inner leaflet of the membrane. This redistribution is referred herein as loss of cell membrane lipid asymmetry (CMLA). In addition to CMLA loss, PNOM is also often associated with reduction in the level of packing of membrane phospholipids and an increase in membrane fluidity.

These alterations play an important role in rendering the cell surface a catalytic platform for the assembly of several clotting factor complexes, such as the tenase and prothrombinase protein complexes. Accordingly, platelet activation is associated with the platelet membrane undergoing PNOM, and these alterations constitute an important factor in normal blood coagulation, as well as in the initiation and/or propagation of abnormal, excessive blood clotting in numerous disorders. These disorders include, among others, arterial or venous thrombosis or thrombo-embolism [e.g., cerebral stroke, myocardial infarction, deep vein thrombosis (DVT), disseminated intravascular coagulation (DIC), thrombotic thrombocytopenic purpura, etc.], unstable atherosclerotic plaques, sickle cell disease, beta-thalassemia, anti-phospholipid antibody syndrome [among others in systemic lupus erythematosus (SLE)], and disorders associated with shedding of membrane microparticles, e.g., neurological dysfunction in association with cardiopulmonary bypass.

Apoptosis is another major situation in which alterations/perturbations of cell membrane take place. Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages. PNOM is a universal phenomenon of apoptosis, it occurs early in the apoptotic cascade, probably at the point of cell commitment to the death process, and has also been shown to be an important factor in the recognition and removal of apoptotic cells by macrophages.

A strong correlation has been recently drawn between PNOM and the potent procoagulant activity of apoptotic cells. PNOM in apoptotic endothelial cells, such as those occurring in atherosclerotic plaques, probably plays an important role in the pathogenesis of thrombotic vascular disorders.

Since apoptosis or thrombosis each has an important role in the majority of medical disorders, it is desirable to have tools for detection of these biological processes and targeting of associated cells. Compounds for selective binding to PNOM-membranes, potentially also performing subsequent entry into and accumulation within these cells having such PNOM-membranes (PNOM-cells) may therefore serve as an important tool for detecting and targeting of imaging agents or drugs to cells undergoing damage or death process, especially by apoptosis, or to platelets undergoing activation.

SUMMARY OF THE INVENTION

In one embodiment of the invention, there is provided a method of detecting PNOM cells within a population of cells, comprising the steps of: (i) contacting the cell population with a PMBC, wherein the PMBC is according to the structure set forth in any of the formulae I-IV; and (II) determining the amount of PMBC bound to cells in the cell population; wherein an amount of PMBC bound to cells, which is significantly higher than the amount bound to control cells, indicates the presence of PNOM-cells within the examined cell population In another embodiment of the invention, there is provided a method for detecting the presence of PNOM-cells in a tissue of an animal, comprising the steps of: (i) administering a PMBC the animal, wherein the PMBC has a structure according to the structures set-forth represented in any of the formulae I-IV; and (ii) determining the amount of PMBC bound to cells in the examined tissue; wherein an amount of compound bound to cells in a tissue, which is significantly higher than the amount of compound bound to cells in a control tissue, indicates that the tissue contains PNOM-cells.

In another embodiment of the invention, there is provided a kit, comprising a compound having a structure according to the structures as set forth in any of the formulae I-IV in a first container; a buffer composition in a second container; and instructions for using the kit for detection of apoptotic cells. The kit may be suitable for use in one embodiment in vitro, on tissue culture, or in another embodiment in vivo, for systemic administration.

In another embodiment of the invention, there is provided a method for screening and/or assessing the efficacy of a drug, wherein the drug is used for the treatment or prevention of a disease associated with an excess of apoptotic cells, or for inducing apoptosis in at least one organ. The method comprises the steps of: (i) administering the drug to an organism having said disease; (ii) administering the compound according to the structure set forth in any of the formulae I-IV to said diseased organism; (iii) obtaining a diseased organ from the diseased organism; (iv) measuring the amount of the compound bound to the diseased organ, through assessment of the amount and/or distribution of fluorescence in the examined tissue; wherein, if the fluorescence is lower than the fluorescence of an organ from a healthy organism, the drug is indicated as efficacious for the treatment or prevention of the disease in which an excess of apoptotic cells is involved, namely apoptosis inhibitor and if the fluorescence is higher than the fluorescence of an organ from a healthy organism, the drug is indicated as efficacious for the inducing apoptosis.

The method described hereinabove are suitable for detection of either spontaneous apoptosis or apoptosis induced by anti-cancer treatment.

In another embodiment of the invention, there is provided a method for screening the efficacy of a drug as an inhibitor of apoptosis or as apoptosis inducer, comprising the steps of: (i) inducing apoptosis in the cell line; (ii) administering the drug which efficacy is being tested; (iii) contacting the cells with a compound according to the structures set forth in any of the formulae I-IV; (iv) detecting the amount and/or distribution of fluorescence of the compound bound to the cells; wherein, if the fluorescence of the cells treated by the drug is lower than the fluorescence of cells not treated by the drug, the drug is indicated as efficacious for the treatment or prevention of the disease in which an excess of apoptotic cells, is involved namely apoptosis inhibitor and if the fluorescence is higher than the fluorescence of an organ from a healthy organism, the drug is indicated apoptosis inducer. The step of administering the drug which efficacy is being tested may be prior or after the step of inducing apoptosis. In each of the methods of the invention, the step of contacting the cells with a compound according to the structures set forth in any of the formulae I-IV may be also before or after the step of administering the drug which efficacy is being tested may be prior or after the step of inducing apoptosis.

In another embodiment, there is provided a method for screening the efficacy of a drug as an inhibitor of apoptosis or as apoptosis inducer, comprising the steps of: obtaining a tissue; inducing apoptosis in the tissue; contacting the cells with a compound according to the structure set forth in any of formulae I-IV; detecting the fluorescence of the compound bound to the tissue; wherein, if the fluorescence of the tissue is lower than the fluorescence in non-treated cells, the drug is indicated as efficacious for the treatment or prevention of a disease in which an excess of apoptotic cells is involved, namely apoptosis inhibitor and if the fluorescence is higher than the fluorescence of an organ from a healthy organism, the drug is indicated as apoptosis inducer.

BRIEF DESCRIPTION OF THE DRAWINGS

FIG. 19: Apoptosis induced by anti-Fas antibody in Jurkat cells; dual staining with DDC and PI; A—control, B—apoptoic, C—a table comparing the efficiency of DDC in detecting apoptosis vs PI.

DETAILED EMBODIMENTS OF THE INVENTION

Figure 1A:
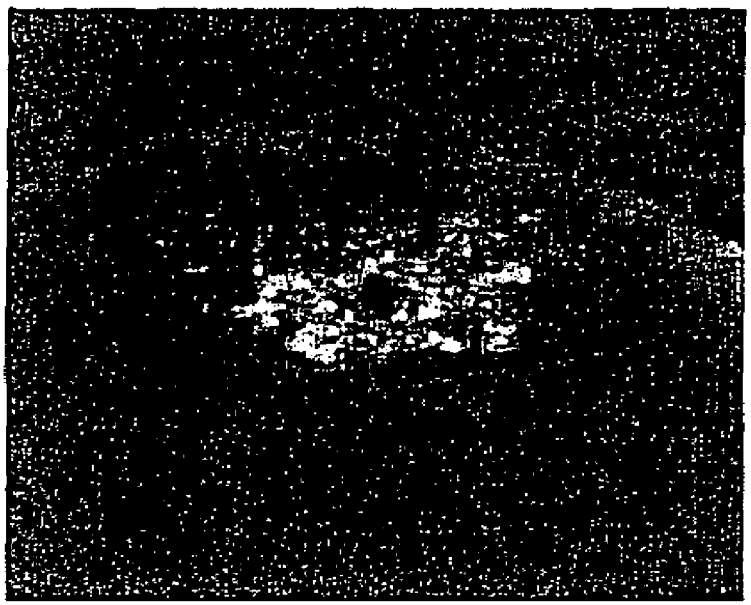
FIG. 1: Detection by DDC of apoptosis induced in lymphoma tumors in mice. (A) control; (B) treated animal.

In one embodiment of the invention, there is provided a method for selective targetting of chemical compounds to cells undergoing perturbation of the normal organization of their plasma membrane, which may be, in an embodiment of the invention, cells undergoing a death process such as apoptosis, or, in another embodiment of the invention, platelets undergoing activation. These cells are designated hereinafter PNOM-cells. The method concerns selective targeting of chemical compounds of the invention to the PNOM-cells, being present or scattered within a cell population or a tissue. The term PNOM for the purpose of the invention refers to a cell membrane featuring at least one of the following:

(i) Scrambling of membrane phospholipids, with reduction of normal asymmetry of distribution of phospholipids between the inner and outer leaflets of the cell membrane;

(ii) Exposure of aminophospholipids on the outer cell surface (mainly exposure of phosphatidylserine and phosphatidylethanolamine);

(iii) Impairment of packing of membrane constituents;

(iv) Impairment of normal distribution of lipids within each membrane leaflet, such as formation of lateral domains, being either enriched or poor in a specific lipid membrane constituent, e.g., phosphatidylserine or cholesterol, respectively The term "perturbed membrane-binding compound" (PMBC) refers to a compound that binds selectively to membranes characterized by PNOM, while by contrast, the compound binds to a much lesser degree to cells which maintain the normal organization of their plasma membrane (normal cells). The ratio of binding is at least 30% higher in the PNOM-cell in comparison to a cell of the same tissue or of the same tissue type which maintains the normal organization of its plasma membrane, and which is therefore defined hereto as a "normal cell".

The compounds used in the invention, termed PMBC, include also pharmaceutically acceptable salts, metal chelates, solvates and hydrates of the compounds, as well as solvates and hydrates of the pharmaceutically acceptable salts. Examples of pharmaceutically acceptable addition salts include inorganic and organic acid addition salts such as, for example without being limited, hydrochloride, hydrobromide, phosphate, sulphate, citrate, lactate, tartrate, maleate, fumarate, mandelate, oxalate, and acetate. Alternatively, pharmaceutically acceptable inorganic and organic base addition salts may be used such as sodium hydroxide, potassium hydroxide, lithium hydroxide, and the like.

The term "significant amount" or "amount which is significantly higher" according to the invention, means that the amount of PMBC bound as to a PNOM-cell is at least 30% higher than the amount bound to a non-PNOM-cell In an embodiment of the invention, an amount of the PMBC bound to a PNOM cell or to a normal cell is reflected by the fluorescence of the PMBC which is bound to the PNOM-cell. In another embodiment of the invention, the amount may be at least 50% higher. In another embodiment, the amount may be at least 60% In another embodiment, the amount may be at least 70% higher In another embodiment, the amount may be at least 80%. In another embodiment, the amount may be at least 90% higher In another embodiment, the amount may be at least 95% higher. In another embodiment, the amount may be at least 150% higher. In another embodiment, the amount may be at least 200% higher. In another embodiment, the may be more than 5 times higher than the binding to a non PNOM-cell. The method for determining the actual amount may vary according to the imaging method and equipment utilized, and according to the organs or tissues examined.

The compounds of the invention may serve in there is provided a method of detecting PNOM cells within a population of cells, comprising the steps of contacting the cell population with a PMBC, wherein the PMBC is according to the structure set forth in any of the formulae I,-IV; and (II) determining the amount of PMBC bound to cells in the cell population; wherein an amount of PMBC bound to cells, which is significantly higher than the amount bound to control cells, indicates the presence of PNOM-cells within the examined cell population.

In another embodiment of the invention, there is provided a method for detecting the presence of PNOM-cells in a tissue of an animal, comprising the steps of: (i) administering a PMBC the animal, wherein the PMBC has a structure according to the structures set-forth represented in any of the formulae I-IV; and (ii) determining die amount of PMBC bound to cells in the examined tissue; wherein an amount of compound bound to cells in a tissue, which is significantly higher than the amount of compound bound to cells in a control tissue, indicates that the tissue contains PNOM-cells.

In another embodiment of the invention, the compound used in the method of detection of the invention has the structure according to formula (I):

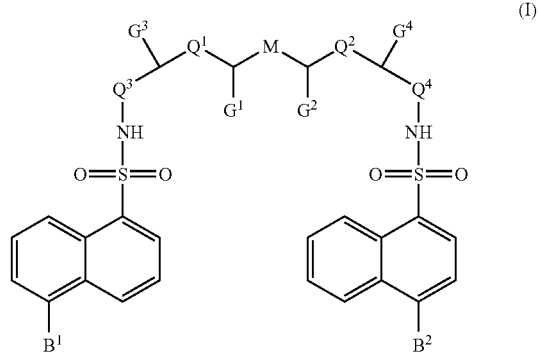

(I)

wherein $G^1$, $G^2$, $G^3$ and $G^4$ groups may be the same or different and are selected independently among hydrogen, COOH, $SO_3H$ and $PO_3H$; at least one of G groups is other than hydrogen;

M is selected among null, O, S, and S—S;

$Q^1$, $Q^2$, $Q^3$ and $Q^4$ groups may be the same or different and are selected among null or $(CH_2)_k$, k being an integer of 1-4;

$B^1$ and $B^2$ may be same or different, selected from hydrogen, $R^6$—N—$R^7$, —OH and —O—$R^6$; wherein $R^6$ or $R^7$ may be same or different, each being selected from hydrogen and $C_1$, $C_2$. $C_3$ or $C_4$ linear or branched, substituted or un-substituted alkyl.

In an embodiment of the invention of the invention, the compound used in the method of detection of the invention has the structure according to formula (II):

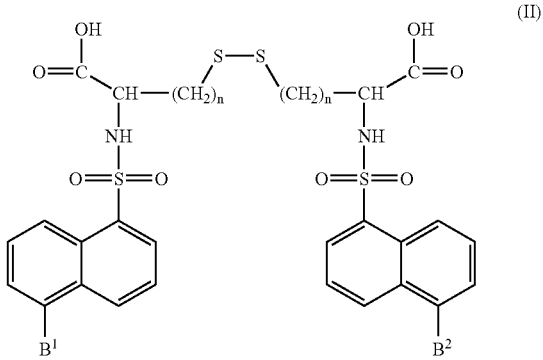

(II)

wherein $B^1$ and $B^2$ may be same or different, selected from hydrogen, $R^6$—N—$R^7$, —OH and —O—$R^6$; wherein $R^6$ or $R^7$ may be same or different, each being selected from hydrogen and $C_1$, $C_2$, $C_3$ or $C_4$ linear or branched, substituted or un-substituted alkyl; and wherein n stands for an integer of 1-3.

In another embodiment, the PMBC used in the present invention has the structure according to Formula (III):

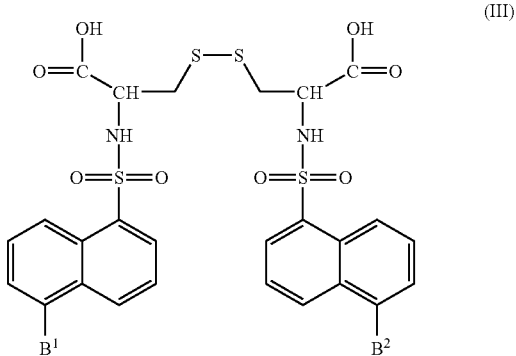

(III)

wherein $B^1$ and $B^2$ may be same or different, selected from hydrogen, $R^6$—N—$R^7$, —OH and —O—$R^6$; wherein $R^6$ or $R^7$ may be same or different, each being selected from hydrogen and $C_1$, $C_2$, $C_3$ or $C_4$ linear or branched, substituted or un-substituted alkyl.

In another specific embodiment, the PMBC used in the present invention has the structure according to Formula (IV), and is designated DDC:

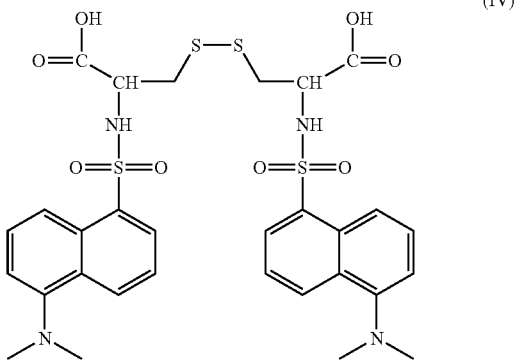

(IV)

In another embodiment of the invention, there is provided a method of detecting PNOM-cells within a population of cells, comprising the steps of: contacting the cell population with a PMBC, wherein said PMBC is according to the structure set-forth in any of the formulae I, II, III or IV; and (II) determining the amount of PMBC bound to cells in said cell population; wherein a bound amount which is significantly higher than the amount bound to control cells indicates the presence of PNOM-cells within the cell population.

In another embodiment of the invention, there is provided a method for detecting the presence of PNOM-cells in a tissue of an animal, comprising the steps of: (i) administering a PMBC the animal, wherein said PMBC is according to the structure set-forth in any of the formulae I, II, I or IV; and (ii) determining the amount of PMBC bound to cells in the examined tissue; wherein an amount of compound bound to cells in the examined tissue, which is significantly higher than the amount of compound bound to cells in a control tissue indicates that the examined tissue contains PNOM-cells.

The present invention also concerns a composition, comprising as an effective ingredient a PMBC as defined above, for the detection of cells comprising perturbed membranes in a sample of biological cells, either in vitro, ex vivo or in vivo. The PMBC in accordance with the detection approach of the present invention is capable of selectively binding to the cells comprising PNOM-membranes present in the assayed sample. The binding may be identified by any means known in the art. The PMBC may have detectable properties of its own such as fluorescence emission, and these detectable properties may be detected, for example, by a fluorescent microscope, or by flow cytometric equipment.

The term "disease characterized by PNOM-cells" or a "diseased animal" refers to a disease or to an animal model of a disease, which one of its manifestations is the perturbation of the normal organization of the cell membranes in tissues inflicted by the disease, e.g., cells undergoing apoptosis. This is not meant to read that this perturbation is necessarily the cause, or the sole effect of the disease, but rather that it is one of its manifestations.

Examples of conditions characterized by PNOM membranes are as follows:

Diseases which are characterized by occurrence of excessive apoptosis, such as degenerative disorders, neurodegenerative disorders (e.g., Parkinson's disease, Alzheimer's disease, Huntington chorea), AIDS, myelodysplastic syndromes, ischemic or toxic insults, graft cell loss during transplant rejection; tumors, and especially highly malignant/aggressive tumors, are also often characterized by enhanced apoptosis, in addition to the excessive tissue proliferation.

Diseases manifested by excessive blood clotting, wherein PNOM occurs during platelet activation, and/or during activation of or damage to other cellular elements (e.g., endothelial cells). These diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

Inflammatory disorders, and/or diseases associated with immune-mediated etiology or pathogenesis, being among others, auto-immune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Atherosclerotic plaques, and especially plaques that are unstable, vulnerable and prone to rupture, are also characterized by cells undergoing PNOM, comprising apoptotic macrophages, apoptotic smooth muscle cells, apoptotic endothelial cells, activated platelets and activated inflammatory cells.

Examples for animal models of disease comprising foci of cell death, are, without being limited, an animal having cancer, wherein the cancer may be without limitation, lymphoma, breast carcinoma, colon carcinoma, glioma or leukemia.

In another embodiment, the animal suffers from ischemia/reperfusion damage, hypoxia, toxic insults, or sepsis a least one of its organs. Examples for modes of tissue damage induced by ischemia or ischemia/reperfusion are: transient middle cerebral artery (t-MCA) occlusion, permanent middle cerebral artery (p-MCA) occlusion, renal artery occlusion, coronary artery occlusion.

The detection of these pathological conditions, disorders or diseases via detection of the associated PNOM may be an aim by itself, simply for diagnosis of the presence of a disease condition in a specific individual. Alternatively, the detection may serve for proving the efficiency of the implementation of an animal model to a certain disease.

The detection may also be carried out in a person or an animal already known to have the disease, or in an animal model for the purpose of evaluating the disease severity and in order to monitor response to various therapeutic modalities. An example for such monitoring is evaluation of response to anticancer therapy. Since most anti-tumor treatments, chemotherapy or radiotherapy exert their effect by induction of apoptosis, detection by a PMBC of therapy-induced apoptosis of tumor cells may substantially shorten the lag period between the time of administration of an anti-cancer treatment and the time of proper evaluation of their efficacy.

(i) Moreover, said detection may be used to monitor adverse effects of anti-cancer treatments. A large part of such adverse effects is due to untoward treatment-induced apoptosis in normal, yet sensitive cells, such as those of the gastrointestinal epithelium or the bone marrow hematopoietic system. Detection by the PMBC of such apoptosis may allow early detection of this untoward tissue damage and better optimization of the treatment protocol.

In addition, said detection may aim at characterization of intrinsic apoptotic load within a tumor, characterization of the level of aggressiveness of a tumor, and detection of metastases, as these conditions are associated with an enhanced intrinsic apoptotic load.

Similarly, the compositions or the compounds of the current invention may be useful in monitoring graft survival after organ transplantation, since apoptosis, potentially detectable by the PMBC of the invention, plays a major role in cell loss during graft rejection.

In addition, said detection may aim at monitoring response to various cytoprotective treatments, and thus aid in screening and development of drugs, capable of inhibiting cell loss in various diseases (for example those recited above) by enabling a measure of evaluation of cell death.

The detection may also take place for basic research purposes, in the study of apoptosis in tissue culture and animal models, and may also help in determining the role of apoptosis in normal development and homeostasis of various tissues, such as in the development of the central nervous system during embryogenesis, as well as during situations such as normal aging.

The method of the present invention may be also used for monitoring the effects of various therapeutic modalities for said diseases or medical conditions, or alternatively for basic science research purposes as explained above. In an embodiment of the invention, there is provided a method for screening and/or assessing the efficacy of a drug, for the treatment or prevention of a disease associated with an excess of apoptotic cells, in at least one organ. The method comprises the steps of (i) administering the drug to an organism having said disease; (ii) administering the compound according to the structure set forth in any of the formulae I-IV to said diseased organism; (iii) obtaining a diseased organ from the diseased organism; (iv) measuring the amount of the compound bound to the diseased organ, through assessment of the amount and/or distribution of fluorescence in the examined tissue; wherein, if the fluorescence is higher than the fluorescence of an organ from a healthy organism, the drug is indicated as efficacious for the treatment or prevention of the disease in which an excess of apoptotic cells is involved.

In another embodiment of the invention, there is provided a method for screening the efficacy of a drug as an inhibitor of apoptosis, or as an inducer of apoptosis comprising the steps of: (i) obtaining a cell line; (ii) inducing apoptosis in the cell line; (iii) administering the drug which efficacy is being tested; (iv) contacting the cells with a compound according to the structure set forth in any of the formulae I-IV; (v) detecting the amount and/or distribution of fluorescence of the compound bound to the cells; wherein, if the fluorescence of the cells treated by the drug is lower than the fluorescence of cells not treated by the drug, the drug is indicated as efficacious for the treatment or prevention of the disease in which an excess of apoptotic cells is involved and if the fluorescence of the cells treated by the drug is higher than the fluorescence of cells not treated by the drug, the drug is indicated as apoptosis inducer In another embodiment of the invention, there is provided a method for screening the efficacy of a drug as an inhibitor of apoptosis or as apoptotic inducer, comprising the steps of: obtaining a tissue; inducing apoptosis in the tissue; contacting the cells with a compound according to the structure set forth in formula I-IV; detecting the fluorescence of the compound bound to the tissue; wherein, if the fluorescence of the tissue is lower than the fluorescence in non-treated cells, the drug is indicated as efficacious for the treatment or prevention of a disease in which an excess of apoptotic cells is involved and if the fluorescence of the cells treated by the drug is higher than the fluorescence of cells not treated by the drug, the drug is indicated apoptosis inducer.

The methods of the invention can be used either in vitro, in vivo, or ex vivo.

The pharmaceutical/diagnostic composition of the invention, comprising the compound represented by the structure as set forth in any of the formulae I-IV of the invention, may be administered by any of the routes, known in the art, being among others oral, intravenous, intraperitoneal, intramuscular, subcutaneous, sublingual, intraocular, intranasal or topical administration. The formulation administered to the examined organism or tissue may be selected in accordance with the desired mode of administration, and may include any known components, e.g. solvents; emulgators, excipients, talc; flavors; colors, etc. The pharmaceutical composition may comprise, if desired, also other pharmaceutically-active compounds which are used to treat the disease, eliminate side effects or augment the activity of the active component. In an embodiment of the invention the concentration of the stock is 2-7 mg/mil and the animal is injected about 30-70 mg/kg of the compound according to any one of the structure set forth in formulae I-IV.

In another embodiment of the invention there is provided a kit for carrying out the methods of the invention. Such kits include, in one or more containers, usually conveniently packaged to facilitate use in assays, quantities of various compositions for carrying out the methods of the invention. The kit may also include instructions on its use. For example, the present invention provides a kit, including a compound of the invention and a first container, packaging material, and instructions for the use of the kit to detect or determine apoptotic cells in a biological sample.

In an embodiment of the invention, there is provided a kit, comprising a compound according to the structure as set forth in any of the formulae I, II, III or IV in a first container; a buffer in a second container; and instructions for using the kit to detect apoptotic cells.

In an embodiment of the invention Reaction the buffer used is HBS (Hepes buffer). In an embodiment of the invention the HBS may contain 10 mM Hepes and 140 mM NaCl.

In an embodiment of the invention, the compound is dissolved in Nappi which is a mixture of $Na_2HPO4$, and $Na_2H_2PO4$. In another embodiment, the concentration of Nappi is 0.02-2.00M. In another embodiment the concentration is 0.1M. In another embodiment of the invention, the concentration is 0.5M. In an embodiment of the invention, the concentration for flow cytometric (FACS) analysis is 100-250 μM. In another embodiment, the concentration for cell staining is 10-50 μM.

EXAMPLES

In order to understand the invention, and to see how it may be carried-out in practice, embodiments of the invention will now be described, in which binding of the compounds of the invention to PNOM-cells, undergoing apoptosis or activation was evaluated. Binding was measured by monitoring the intensity of the intrinsic fluorescence of the compounds, either by fluorescent microscopy or by flow cytometric (FACS) analysis. In an embodiment of the invention, the compound used is DDC, which is represented by the structure set forth in formula IV of the invention.

Experimental Procedures

A. Administration of DDC in-vivo: Injection of 200 μl of DDC intravenously. Following 1-2 hours, animal is sacrificed, and the desired organ is placed in a test tube or on a small plate, suitable for liquid nitrogen freezing. The plate is then covered with an aluminum foil, and transferred to liquid nitrogen. Following 5-30 minutes the specimen is being frozen to −80° C. and kept at −80° C. for at least 16 hr.

B. Analysis of the Specimen:
a. Whole organ imaging Ex-vivo whole organ fluorescence imaging may be carried out on freshly excised specimen, that can be analyzed under a stereomicroscope (such as Leica MZ FL III, Leica Switzerland). DDC may be visualized using $360_{ex}$ and $>420_{em}$ nm filter set. Emitted fluorescence can be imaged using appropriate camera and software, such as a Leica DC 300F Distal camera and images can be processed and analyzed by Leica QWin Lite software.
b. Histological analysis, from the frozen organ or tissue, 4 μm cryosections are prepared on slides. Analysis of the tissue sections can be performed using a fluorescence microscope with a UV filter characterized by excitation at 360-370 nm (band pass) and emission at 420 nm (barrier filter) In case that staining of the examined tissue is desired, the following procedures can be applied:

For a correlation with the presence of apoptotic cell nuclei, a parallel section can be used for TUNEL staining, using apoptosis detection kit (such as ApopTag Fluorescein Kit, Intergen company Purchase, N.Y.). For a correlation with the standard histological H&E staining, a consecutive slide can be use for morphological evaluation of the DDC positive cells.

C. Detection of Apoptosis In-vitro
DDC powder is dissolved in the appropriate volume of buffer (the solution is stirred at RT or 37° C. until it is clear).
A. Analysis by flow cytometry (FACS), 1. Cell Preparation
   a. Non Adherent Cells
1. Inducing cells to undergo apoptosis. A negative control should be prepared by incubating cells in the absence of apoptosis induction agent.
2. Washing the cells and adjusting the number of cells to $1\times10^7$/ml in PBS.
3. Transferring 30 μl from the cell suspension to a suitable test tube for FACS analysis.
4. Adding 260 μl of PBS and 5 μl of DDC to the tube and incubating for 15 minutes at room temperature (RT), protected from light.
5. Adding 5 μl of Propidium Iodide (PI) and perform FACS analysis.
   b. Adherent (Attached) Cells
1. Seeding cells on suitable petri dishes, and inducing apoptosis.
2. After treatment, trypsinizing the cells, washing, counting and adjusting to $1\times10^7$/ml in PBS.
3. Adding 260 μl of PBS and 5 μl of DDC to the tube and incubating for 15 minutes at room temperature (RT), protected from light.
4. Performing FACS analysis.
   c. Attached and Detached Cells Several death inducers for adherent cells (in specific concentration or time exposure) may result in two sub-populations of cells: cells that are still attached and cells that undergo detachment from the dish following apoptosis.
1. Seeding cells on suitable petri dishes. Inducing cells to apoptosis.
2. After treatment, collecting the cells that may have detached from the growth surface during apoptosis induction. This may performed by gently agitating the dish and transferring the cell culture supernatant into a sterile polystrene test tube (15 ml).
3. Adding trypsin solution to the dish.
4. Combining the trypsinized cells with the detached cells and pellet the cells.
5. Washing, counting and adjusting to $1\times10^7$/ml in PBS.
6. Adding 260 μl of PBS and 5 μl of DDC to the tube and incubating for 15 minutes at room temperature (RT), protected from light.
7. Adding 5 μl of Propidium Iodide (PI) and perform FACS analysis 2. Analysis by Flow Cytometry
Analyzing DDC accumulation by flow cytometry using FACS apparatus that includes a UV laser. For DDC analysis: the UV detector excitation is at 356 nM and the emission is at 530 nM with a band pass of ±15 nM. For PI analysis: excitation is at 488 nM and the emission is at 575 nM with a band pass of ±13 nM. The population should be separated into three groups: live cells will show a low level of fluorescence (background), apoptotic cells will show higher UV fluorescence and necrotic cells will show both red and higher UV fluorescence.

3. Detection of DDC by Fluorescent Microscopy
For microscopic analysis the concentration of cells should be within $1\text{-}2\times10^7$/ml. DDC analysis does not require any fixation. If fixation is needed, it should be performed after DDC staining.
1. Adjusting the cells to $1\text{-}2\times10^7$/ml in buffer.
2. Transferring 96 μl from the cell suspension to an eppendorf and staining the cells by adding 4 μl from the DDC solution. Incubating for 10-40 minutes at RT protected from light.
3. A double labeling could be conducted with PI, if desired. In such a case, 1 μl is added from the PI solution.
4, Placing the cell suspension on a glass slide. Covering the cells with a glass coverslip. Alternatively, for analyzing adherent cells, cells may grow directly on coverslip. Staining the cells by incubation with DDC (4 μl of DDC/96 μl buffer reaction) or 10-40 minutes and PI (1 μl). Covering the slide with a coverslip and visualizing the cells. If desired, at that point the cells can be washed and fixed in 1% formaldehyde before visualization. Mounting should be done in a solution of 50% glycerol/PBS (v/v).

5. Observing the cells under fluorescent or confocal microscope equipped with the appropriate UV filter (excitation at 360-370 nm, band pass, and emission at 420 nm, barrier filter. Using a Triple filter (Hoechst/FITC/Texas Red) allows concomitant observation of both DDC and PI.

Quantitative Assay for DDC Accumulation using Fluorescene Spectroscopy

Uptake of DDC into apoptotic/necrotic cells can be evaluated quantitatively by measuring the accumulation of fluorescence levels within the cells.

Quantitative Analysis for DDC Accumulation In-vivo

Uptake of DDC into apoptotic/necrotic cells can be evaluated quantitatively by measuring the accumulation of fluorescence levels within the cells/tissue. However, detection of apoptosis/necrosis by fluorescent spectroscopy depends on labeling efficiency, which varies among cell types, cell number and sensitivity of the detection instrument used (fluorescence plate reader). Investigators should titrate the DDC to accommodate their particular tissue or research conditions.

Extraction of DDC uptake compound from cytosolic extracts of organs or tissues for quantitative measurement of DDC uptake:

a. Excising the relevant organ from animals, that were previously injected with DDC.
b. Weighting the organs and homogenize using tissue homogenizer in a cold Buffer-Hepes
c. Following total homogenization, centrifuging the sample at 13,800 rpm for 20 min at 4° C. and transferring the supernatant to a new test tube.
d. Repeating step c and taking the supernatant for quantitative fluorescence evaluation. Alternatively, the supernatant can be stored at −80° C. until use.
e. Placing a sample of 100 ul of organ suspension into each of three wells of a black to microtiter plate.
f. Measuring the fluorescence intensity of DDC (excitation 360 nm, emission 535 nm) using a fluorescence plate reader.

Creating a calibration curve for the fluorescence plate reader using serial dilution of the DDC compound: 1:10, 1:20, 1:40, 1:80, 1:160, 1:320, 1:640, 1:1280.

Quantitative Analysis for DDC Accumulative In-vivo

Uptake of DDC into apoptotic/necrotic cells can be evaluated quantitatively by measuring the accumulation of fluorescence levels within the cells. However, detection of apoptosis/necrosis by fluorescence spectroscopy depends on labeling efficiency, which varies among cell types, cell number and sensitivity of the detection instrument used (fluorescence plate reader). Investigators should titrate the DDC uptake to accommodate their particular cell line or research conditions.

Extraction of DDC compound from cells for quantitative measurement of DDC uptake.

A. Cells Staining
a. Inducing apoptosis according to your specific protocol, adjust the cells to a concentration of $10^7$/ml.
b. For cell labeling-transferring 900 µl aliquot of apoptotic or control cells in triplicates.
c. Adding 100 µl of DDC directly to the cell suspension. Gently mix and incubate the cells for 40 in at R.T. protecting the test tubes from light.
d. Incubating the cells on ice for 20 min and spin down the cells at 1600 RPM for 10 minutes in a cold centrifuge. Discard supernatant.
e. Washing the cells by addition of 1 ml of PBS buffer to the pellet mix.
f. Repeating step 5. Add 300 µl of cold buffer Hepes.

B. Cell Extraction
a. Homogenizing the cells (using homogenizer) in 300 µl cold Buffer-H.
b. Following total homogenization, centrifuge the sample at 13,800 rpm for 20 min at 4° C. and transferring the supernatant to a new test tube.
c. Placing a sample of 30 µl of cell suspension into each of three wells of a black microtiter plate.
d. Measuring the fluorescence intensity of DDC (using a UV filter; excitation at 360 nm, emission at 535 nm) using a fluorescence plate reader.

For controls, wells containing PBS only and unlabeled cells may be used.

Preparation of calibration curve: linear calibration curve should be determined using serial dilution of the DDC compound starting from 1:10, 1:20, 1:40, 1:80, 1:160, 1:320, 1:640, 1:1280.

Example 1

Detection by DDC of Tumor Cell Apoptosis in Lymphoma-bearing Mice

DBA/2 mice (8 weeks old males), were injected subcutaneously with 106 of L5178-S (LY-S) murine lymphoma cells and were examined daily for tumor growth. When the tumor reached 6-8 mm in diameter (approximately ten days after tumor cell implantation), chemotherapy, Taxol (20 mg/kg), was administered intrarperitoneally. 24 hours after Taxol administration, animals were injected intravenously with DDC and sacrificed two hours later. Tumors were excised and subjected to whole organ imaging using stereomicroscope (A) or snap frozen and and cryosections from control (B) or Taxol treated (C) animals were prepared.

Figure 1B:

As can be seen in FIG. 1, accumulation of DDC in the treated tumor can be seen in whole tumor imaging (A) as well as in the histological slides. A marked increase of DDC uptake into tumors can be seen following treatment with Taxol; (C) taxol treated animals in comparison to (B) control animals.

Example 2

Quantification Cell Death in Lymphoma, Induced by Radiotherapy; Detection by DDC Murine lymphoma model was established using DBA/2 mice injected subcutaneously with L5178-S murine lymphoma cells. Tumor treatment, by multiply fractionated X-irradiation (3 fractions of 6 Gy/day), started when the tumor reached in diameter 6-8 mm (approximately ten days after tumor implantation). At different time points (24, 48 or 72 hours) following irradiation, mice were injected with DDC for 2 hours. Tumors were harvested from control and radiation-treated animals and processed for quantitative analysis of DDC uptake into the tumor.

Figure 2:
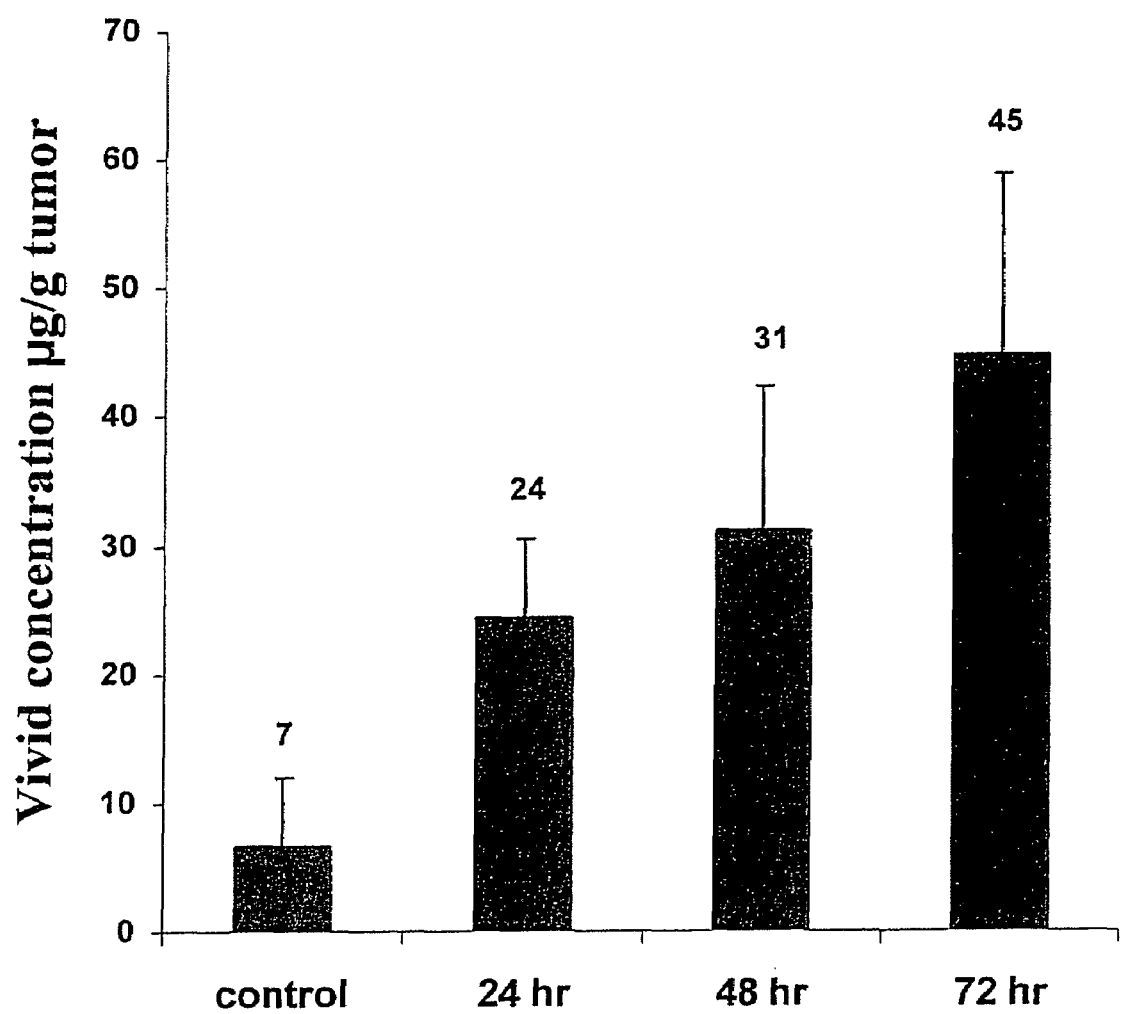
FIG. 2: Quantification using DDC of cell death induced by radio-therapy in lymphoma.

Results of quantitative analysis of DDC uptake into the tumor (expressed as 1 g/g tumor tissue) are presented in FIG. 2. DDC uptake values obtained (mean±sd) were 3.68, 4.69 and 6.74 times higher over the control mean values, respectively. The results show the ability of DDC to detect apoptotic cells in lymphoma tumors in radiation in treated animals.

Example 3

Induction of Apoptosis in Mice Bearing Breast Carcinoma, Detection by DDC

MCF-7 cells (106 cells) were injected subcutaneously beneath two of the nipples of female ICR nude mice (8 weeks old, 18-20 gr). A pellet of 0.72 mg of β-estradiol (Innovative Research of America, Sarasota, USA) was transplanted subcutanously on the neck of the animal. Five to six weeks after cell injection, mice were irradiated with x rays, and exposed to two doses of 8 Gray (24 hours between the doses). 24 hours after the second dose, DDC was injected i.v. and the mice were sacrificed 2 hours later. Tumors were excised and frozen in liquid nitrogen and sectioned for histological evaluation.

Figure 3A:
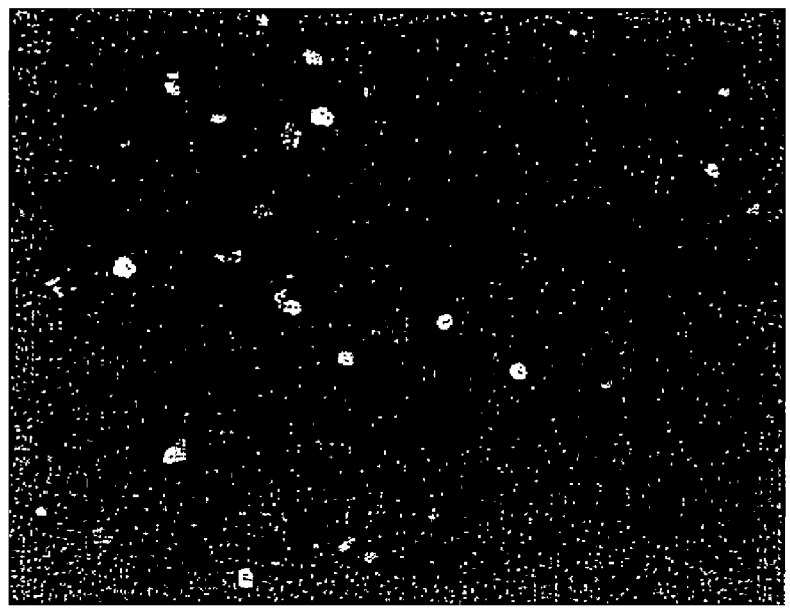
FIG. 3: Detection by DDC of apoptosis induced by irradiation in breast carcinoma in mice. (A) non-treated; (B) following irradiation.
Figure 3B:
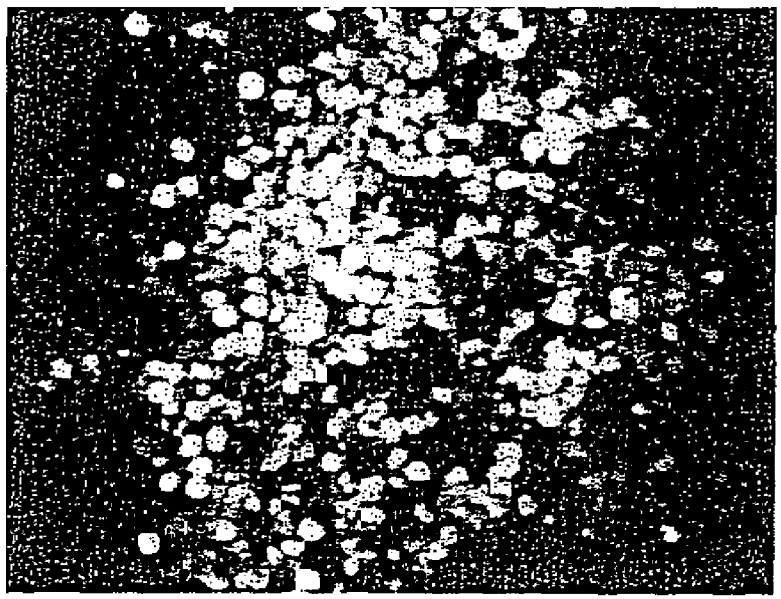

As can be seen if FIG. 3, increased uptake of DDC into single cells of the tumor can be seen following irradiation in comparison to non irradiated cells. The results show the ability of DDC to detect apoptotic cells in carcinoma tumors in radiation in treated animals.

Example 4

Figure 4A:
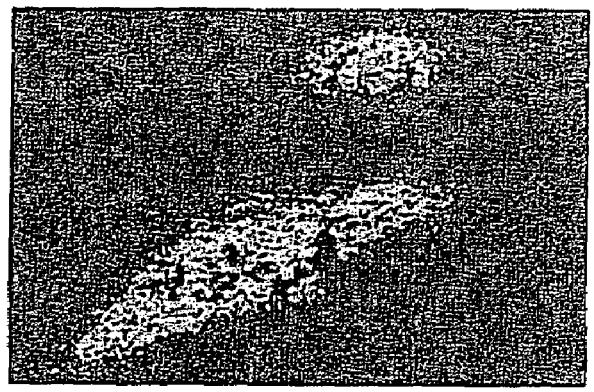
FIG. 4: Induction of apoptosis in c26 colon carcinoma in mice: Correlation between DDC binding (A) and staining with TUNEL (B) and H&E (C).
Figure 4B:
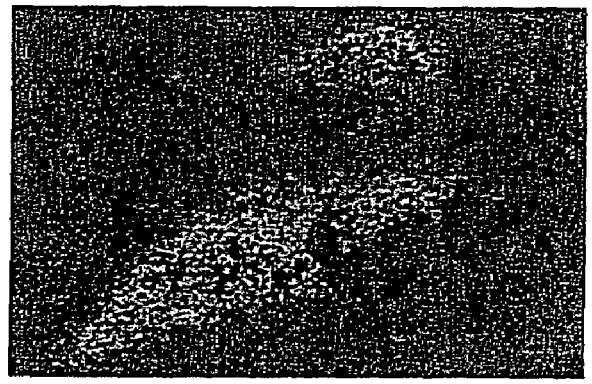
Figure 4C:
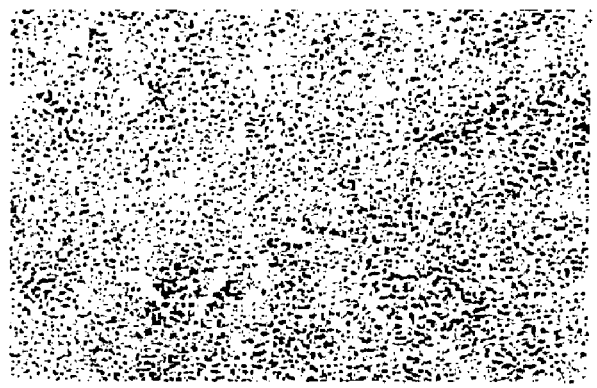

Induction of Apoptosis in Colon Carcinoma: Correlation Between DDC Binding and Staining with TUNEL and H&E Balb/c mice (8-12 weeks old males) were injected subcutaneously with $4 \times 10^5$ of C26 colon carcinoma cells and were examined daily for tumor growth. At day 18 the mice received one dose of Doxorubicin (20 mg/kg). Forty eight hours after Doxorubicin administration, animals were injected intravenously with DDC (as detailed in DDC protocols II-A) and sacrificed two hours later. Consecutive slides were prepared and were subjected to different staining procedures (as detailed in DDC protocol II-B): Slides were analyzed under fluorescence microscope using UV filter for DDC (A), NIBA filter for TUNEL staining method (B) or by light microscopy for H&E (C). As can be seen in FIG. 4, DDC staining (A) highly correlated with both H&E (C) and TUNEL (B) staining and emphasized the selectivity and specificity of detection of apoptotic cells. However, both TUNEL and H&E staining can not be performed in-vivo, and are performed only in-vitro.

Example 5

Figure 5:
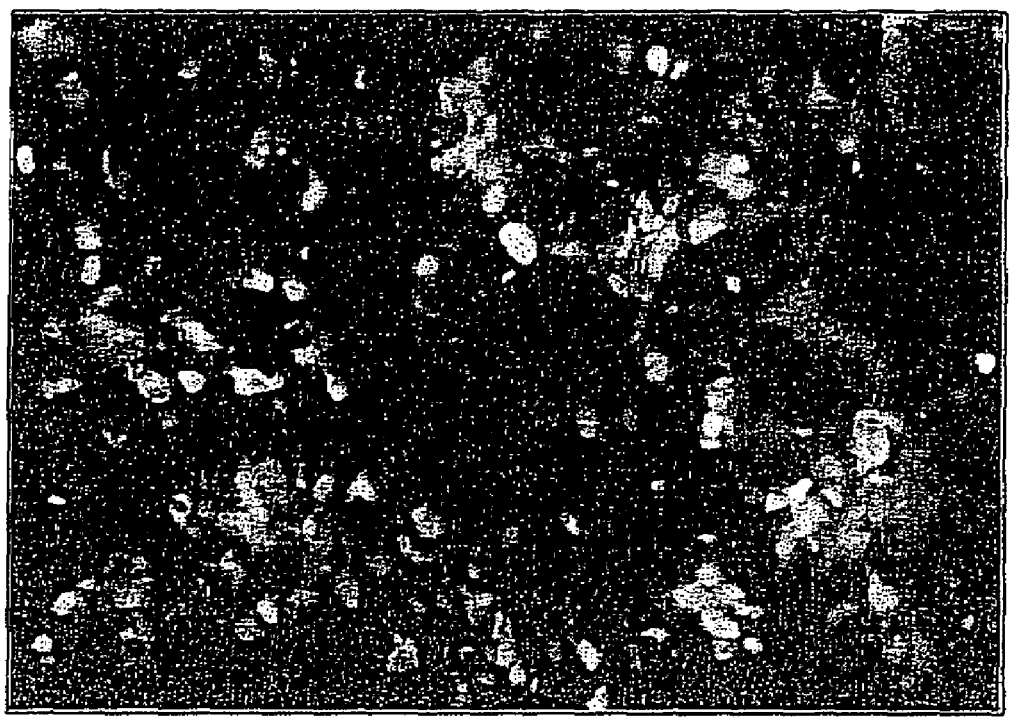
FIG. 5: Induction of apoptosis in mice bearing lung metastases of c26 colon carcinoma, detection by DDC.

Induction of Apoptosis in Mice Bearing Lung Metastases of c26 Colon Carcinoma, Detection by DDC C26 cells (ATCC, $2 \times 10^5$/mouse) were injected i.v. into male Balb/c mice, 8-10 weeks old, 20-22 g. After 30 days, lung metastases were formed, and chemotherapy by doxil was started. The mice received two doses of 20 mg/kg of doxil, with an interval of 144 hours between the two doses. 144 hours after the second dose, DDC was injected i.v and the mice were sacrificed 2 hours later. Tumors were excised and frozen in liquid nitrogen and sectioned for histological evaluation. As demonstrated in FIG. 5. DDC 20 detected apoptotic cells in the lung metastases that responded to doxil treatment. Apoptotic cells were identified by DDC in multiple foci that were scattered throughout the lungs.

Example 6

Accumulation of DDC in Apoptotic Cells of Glioma Following Irradiation

C6-Glioma cells (ATCC) were injected into the right caudate nucleus of CBA/ca mice. Tumors were allowed to grow for 9 days, wherein animals were subjected to radiation (one dose of 6 gray). Twenty hours latter, mice were injected i.v. with DDC and the mice were sacrificed two hours later. Brains were excised and frozen in liquid nitrogen, sectioned for histological evaluation.

Figure 6:
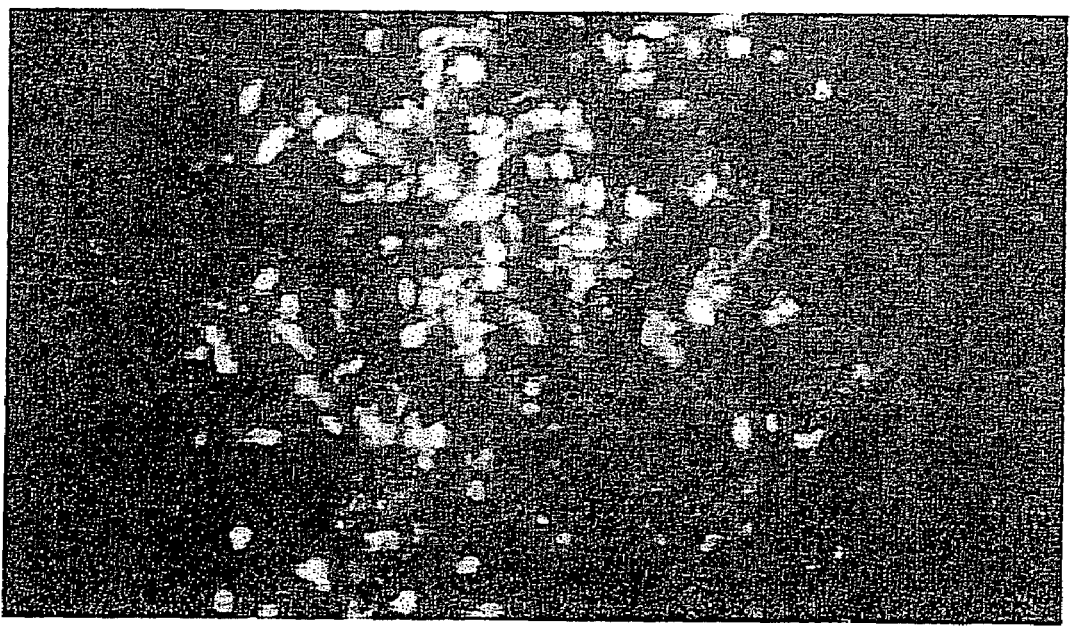
FIG. 6: Accumulation of DDC in apoptotic cells in brain glioma following irradiation.
Figure 7A:
FIG. 7: Induction of apoptosis in BCL1 bone marrow cells following chemotherapy, detection by DDC; non-treated group (A)×200 (B)×400; chemotherapy treated mice (C), (E)×200; (D), (F)×400.
Figure 7B:
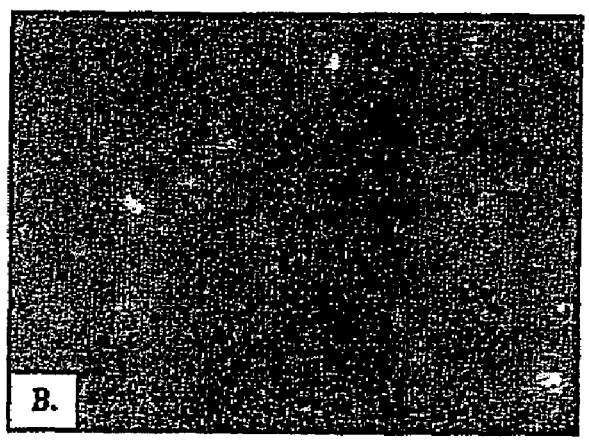
Figure 7C:
Figure 7D:
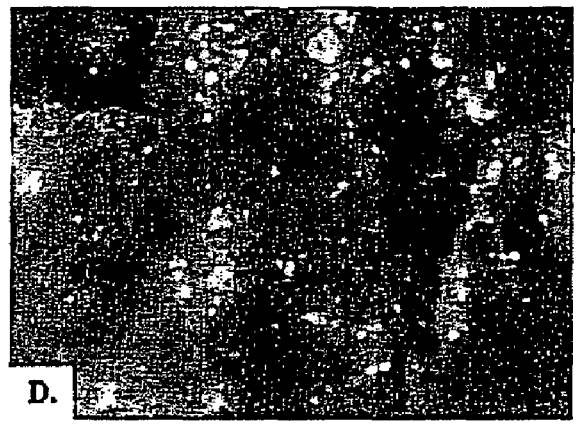
Figure 7E:
Figure 7F:

As is demonstrated in FIG. 6, DDC specifically and selectively labeled cells undergoing cell death within the glioma tumor, while not binding to viable tumor cells or normal brain tissue. Labeling by DDC was at the single-cell level and was correlated with H&E staining (not shown). DDC labeling within the tumors was detected only in animals subjected to the anti-cancer treatments, reflecting specific tumor cell death in response to the therapy. Accordingly, this experiment suggest that DDC may detect cells undergoing cell death within the glioma tumor as well as their response to anti-cancer treatement.

Example 7

Induction of Apoptosis in BCL1 Bone Marrow Cells Following Chemotherapy, Detection by DDC Balb/C mice were injected with carcinogenic B-cell lymphocytes (originated from a colony of Dr. R. Kallman, Warnke et al., 1979) to induce leukemia. At the peak of the illness, when the number of lymphocytes in the Peripheral Blood Lymphocyte (PBL) sample increased by three to four over the normal count, a combination of Cyclophosphamide (300 mg/kg) and Taxol (20 mg/kg) was injected to the experiment group. DDC was injected i.v. 24 hr following chemotherapy and after 2 hr bone marrow samples were taken for histology.

As can be seen in FIG. 7, whereas no fluorescent labeling is demonstrated in the non-treated group (A)×200 & (B)×400, a significant number of apoptotic/necrotic cells are labeled following chemotherapy treatment (C) & (E)×200 & (D) & (F)×400 suggesting the ability of DDC to detect apoptotic/ necrotic following chemotherapy treatment.

Example 8

Induction of Apoptosis in Epithelial Cells of the Small Intestine Following Chemotherapy, Detection by DDC Chemotherapy treatment is not selective to tumor cells, but can also affect other organs/tissue within the body as a side effect. The use of DDC, enables monitoring also the non-selective side effect on other organs. Such side effects may be detected by DDC in the small intestine, in which the epithelial cells are affected by the chemotherapy. Balb/c mice received combined chemotherapy of Cyclopliosphamide (6 mg/kg) and Taxol (20 mg/kg) and following 48 hr DDC was injected i.v. (as detailed in DDC protocols II-A). Two hours later mice were sacrificed and pieces (of 1 cm) from the small intestine were excised and frozen in liquid nitrogen and sectioned for histological evaluation.

Figure 8A:
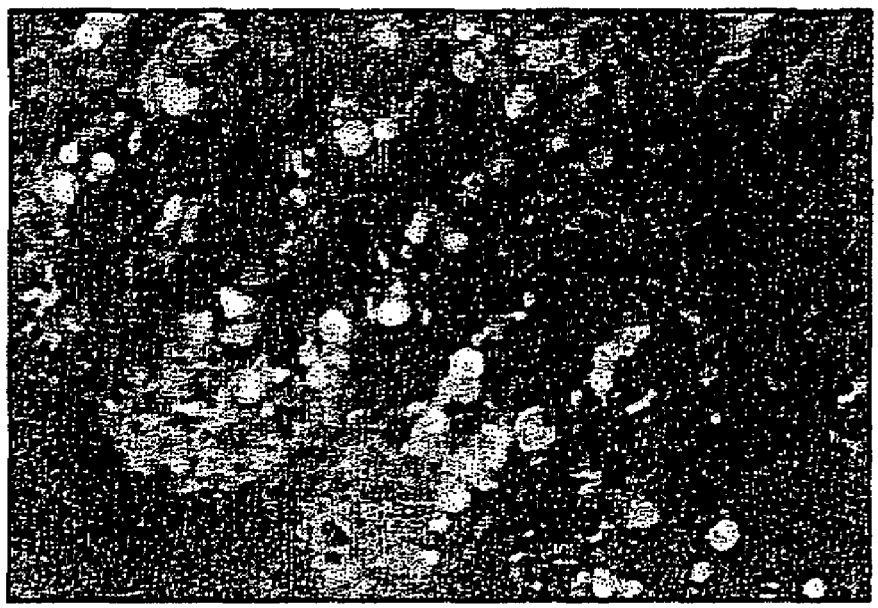
FIG. 8: Induction of apoptosis in epithelial cells of the small intestine following chemotherapy, detection by DDC; (A) DDC, (B) H&E.
Figure 8B:

As is exemplified in FIG. 8, increased uptake of DDC (A) into single epithelial cells can be seen following chemotherapy in correlation with H&E staining (B).

Example 9

DDC Staining of Ischemic Damage Following Transient MCA Occlusion in Mice

Figure 9A:
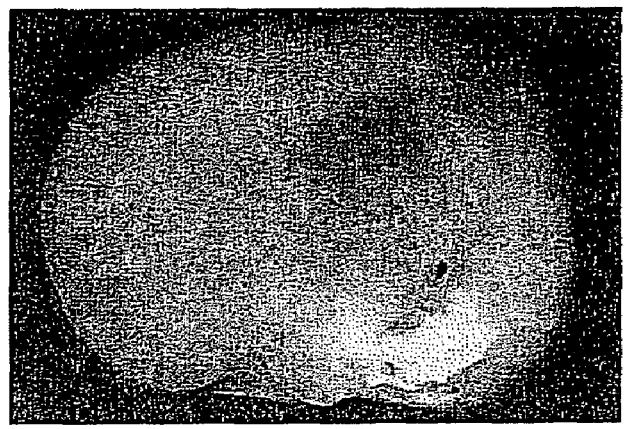
FIG. 9: DDC staining of ischemic damage following transient middle cerebral artery (MCA) occlusion in mice; (A) coronal section, (B) DDC staining, (C) H&E staining.
Figure 9B:
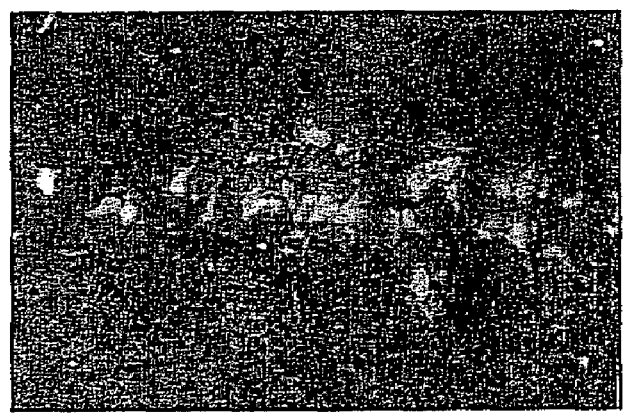
Figure 9C:

Transient focal ischemia was induced by middle cerebral artery (MCA) occlusion and reperfusion. Briefly, rats were anesthetized and maintained with a gas mixture of 98.5% air and 1.5% halothane. A 5-0 siliconized nylon thread was inserted to occlude the origin of the right MCA. After 2 hours (2 h) of MCA occlusion, the thread was removed to allow reperfusion. At 22 hours from MCA occlusion, neurological score was assessed and DDC was injected I.V. (as detailed in DDC protocols II-A) for a successive 2 h before sacrificing the animals. At 24 h from induction of the injury, rats were over-dosed by anesthesia, and brains were removed into liquid nitrogen for farther histopathology. As is seen in FIG. 9, ex-vivo whole organ image of a coronal section (A) that was obtained under stereomicroscope showed the high intensity staining of the ischemic core, close to the MCA origin reflecting the severity of the damage. No staining was detected in the area around the ischemic core as well as in the non-damaged contra-lateral hemisphere. DDC staining can be seen in hippocampal area only at the damaged neuronal cells (B) but not in the intact cells surrounding the damage. The same area is also stained by H&E demonstrating the existence of damaged "red neurons" (C). Magnifications were: ×1.8 in A, ×400 in B&C.

Example 10

A Permanent Ischemia by MCA Cauterization, Detection by DDC

Figure 10A:
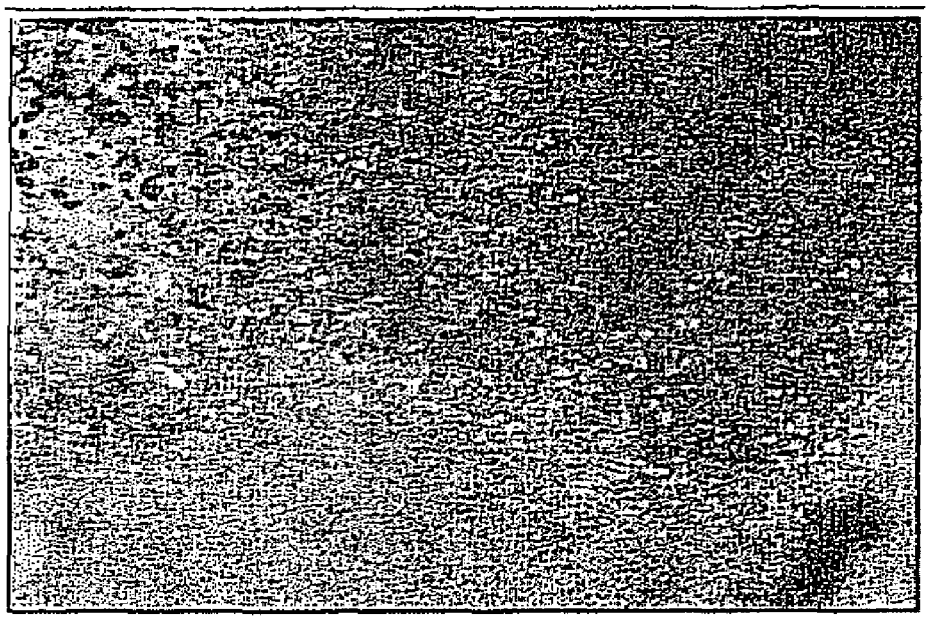
FIG. 10: Detection by DDC of ischemic damage following permanent MCA occlusion in mice; (A) DDC, (B) H&E.
Figure 10B:
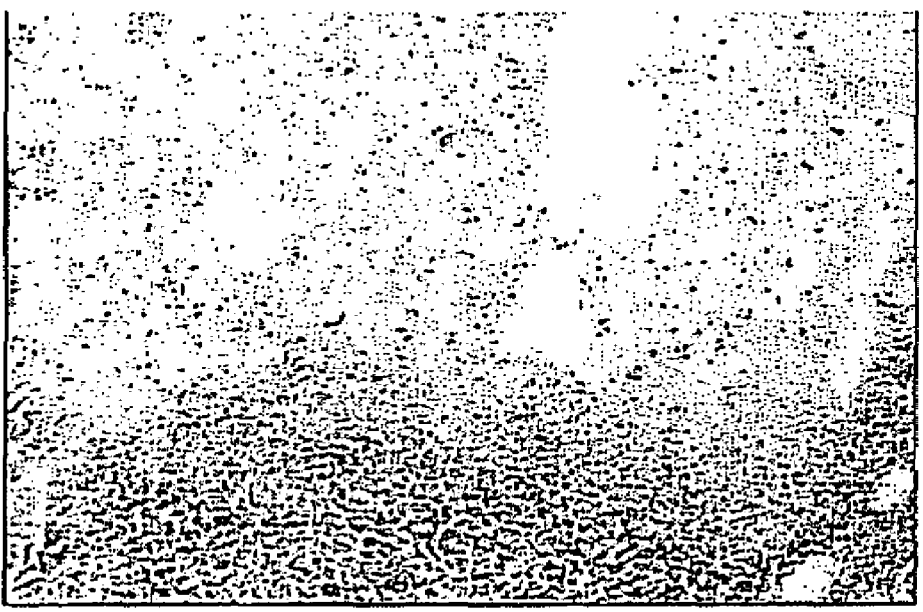

A permanent ischemia by MCA cauterization was induced in Balb/c mice (Harlan laboratories). Mice were anesthetized, and ischemia was induced through a subtemporal approach. The cranyotomy was performed allowing exposure of the MCA to further cauterization 22 hours from the insult, DDC was injected i.v. (as detailed in DDC protocols II-A). At 24 hours from induction of the injury, mice were over-dosed by anesthesia, and brains were removed into liquid nitrogen for farther histopathology. As is demonstrated in FIG. 10, DDC staining of single neurons (A, B) was in high correlation with H&E staining of the adjacent slides (C, D), emphasizing the similarity between DDC staining and pathological changes occurring in the ischemic region.

Example 11

Induction of Apoptosis Following Traumatic Brain Injury (TBI) in Mice, Detection by DDC TBI model was performed on Balb/C, 8-9 weeks old, according to the protocol detailed in Yun Chen et al., 1996. 24 hr after the traumatic injury the mice were injected with DDC and following 2 hr the brain was excised, freezed in liquid nitrogen and sectioned for histological evaluation.

Figure 11:
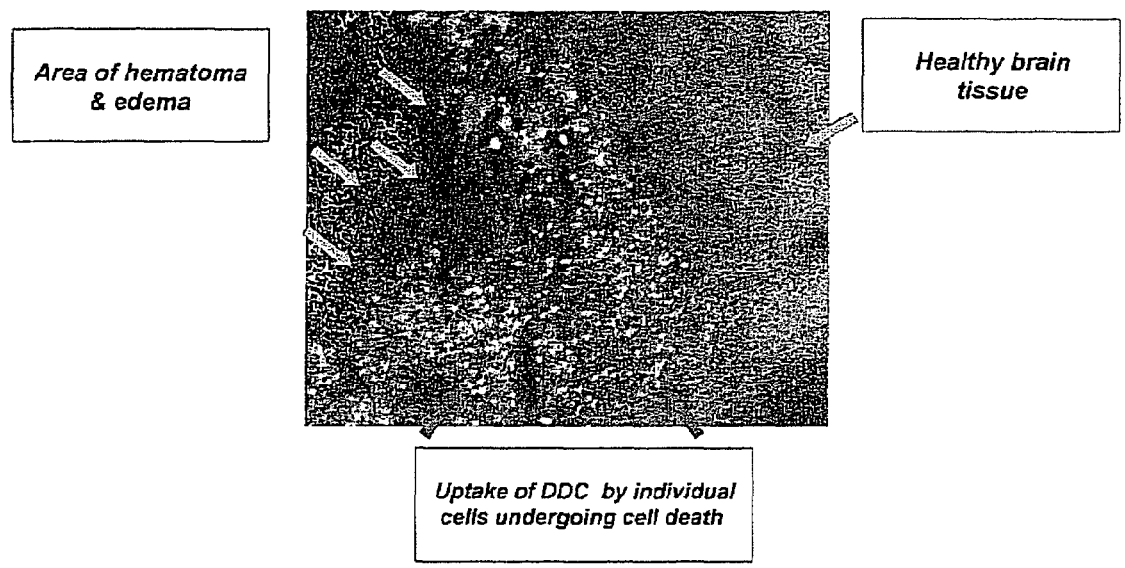
FIG. 11: Induction of apoptosis following Traumatic Brain Injury (TBI) in mice; detection by DDC, 24 hours post trauma.
Figure 12A:
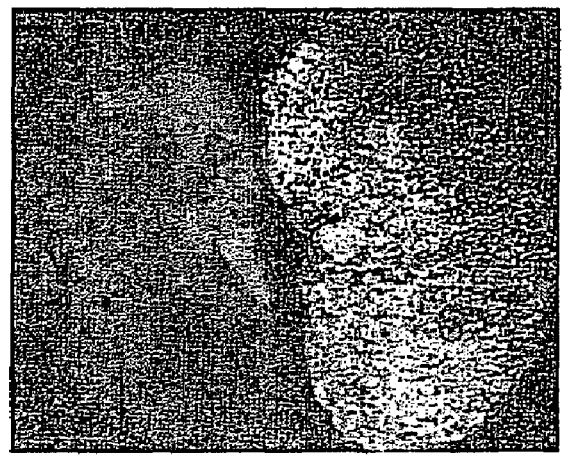
FIG. 12: Detection by DDC of renal cell injury: correlation with histopathology; (A) assessment ex vivo, following systemic administration of DDC left side-sham, right side ischemic kidney; (B&C) localization of DDC in cells undergoing cell death, correlation with H&E staining; (D&E) localization of DDC in cells undergoing cell death, correlation with TUNEL.
Figure 12B:
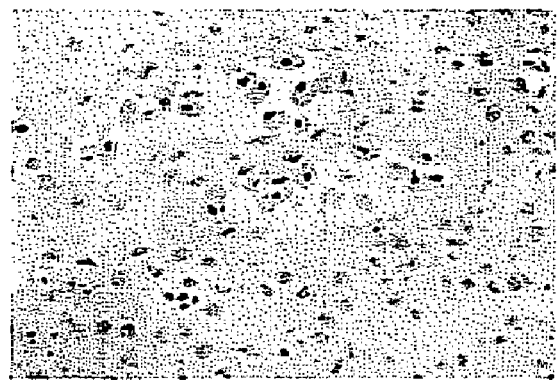
Figure 12C:
Figure 12D:
Figure 12E:
Figure 13A:
FIG. 13: Focal uptake of DDC in the septic kidney of mice: correlation with H&E and TUNEL staining; (A) & (C) DDC, (B) H&E and (D) TUNEL
Figure 13B:
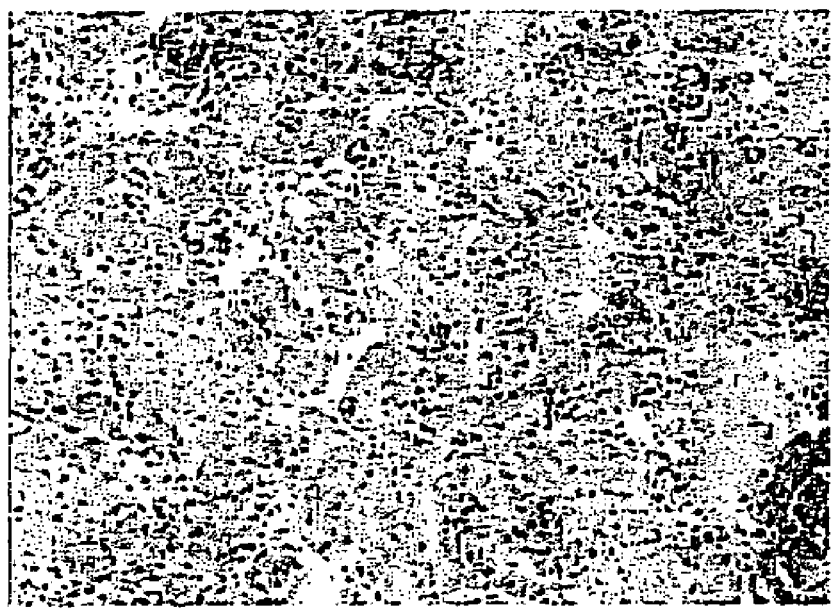
Figure 13C:
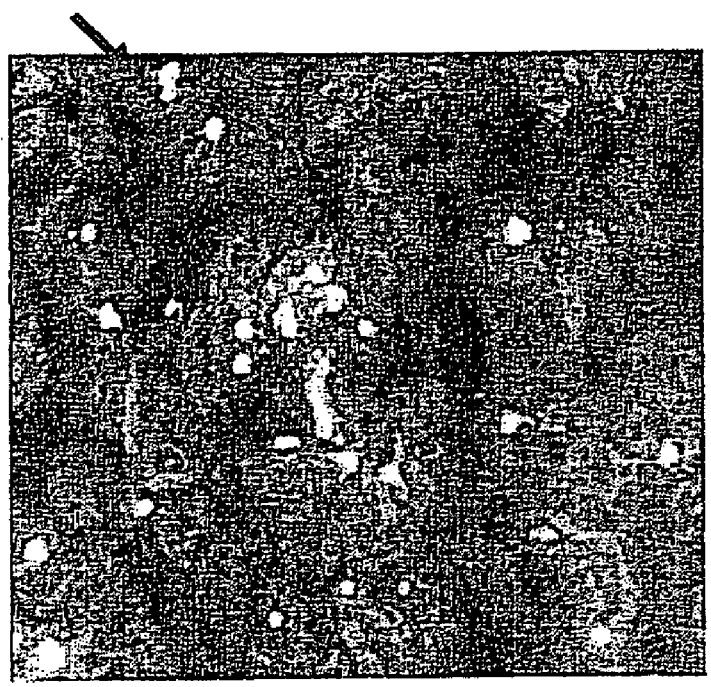
Figure 13D:
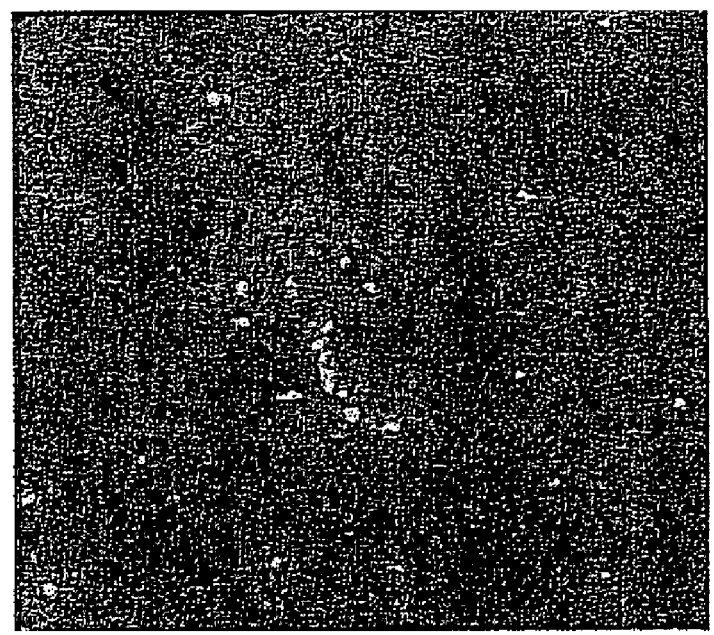

FIG. 11 shows analysis of the sections were analyzed under fluorescence microscope using UV filter for DDC. DDC staining correlated with H&E staining, emphasizing the selectivity and specificity of DDC to the injured area. The arrows point to individual neuronal cells undergoing apoptosis in area surrounding the damaged core.

Example 12

Renal Cell Injury Detection by DDC: Correlation with Histopathology

Renal tubular cell apoptosis was induced by Ischemia-Reperfusion model. Operative procedures were performed in male Sprague-Dawley rats, weighing 180-250 g rats under general anesthesia. Renal ischemia was induced by unilateral left renal artery clamping, using a small nontraumatic vascular clamp, for 45 minutes. The contralateral untreated kidney from the same animal was designed as kidney from sham-operated control. Reperfusion was initiated by removal of the clamp. Twenty hours after the onset of reperfusion, animals were injected intravenously with DDC and four-hours later, both kidneys were excised, frozen in liquid nitrogen and subjected to analysis.

FIG. 12 shows ex-vivo whole organ fluorescence imaging that was carried out on freshly excised kidneys. (A) Significant increase in DDC uptake could be seen in the left ischemic kidney compared with the right control kidney. Correlation between DDC staining of apoptotic cells and H&E is demonstrated in (B) & (C). Correlation between DDC staining and TUNEL is demonstrated in (D) & (E). Several cells were stained with DDC but were negative for TUNEL staining (E, arrow head) emphasizing that detection of apoptotic cells by DDC may precede its detection by TUNEL.

Example 13

Focal Uptake of DDC in the Septic Kidney of Mice: Correlation with H&E and TUNEL Staining The cecum of anesthetized mice was isolated, ligated distal to the ileocaecal valve, and punctured twice with 26-gauge. Twenty-four hours later mice were injected i.v. with DDC and two hours afterwards kidneys were removed and frozen in liquid nitrogen. Histological sections were prepared and subjected to analysis.

As is shown in FIG. 13, most apoptotic cells appeared to be tubular epithelial cells. Focal tubular cell injury is not well defined by routine H&E staining (B), however they were clearly identified by DDC staining (A & C). Correlation with TUNEL (D) emphasized that DDC detected early apoptotic cells where TUNEL staining is still negative (arrow). Correlation with H&E staining emphasized the clear image obtained with DDC, while H&E provided vague and nonsensitive picture of tissue damage.

Example 14

Radiocontrast-induced Distal Tubular Necrosis Model, Detection by DDC

Figure 14:
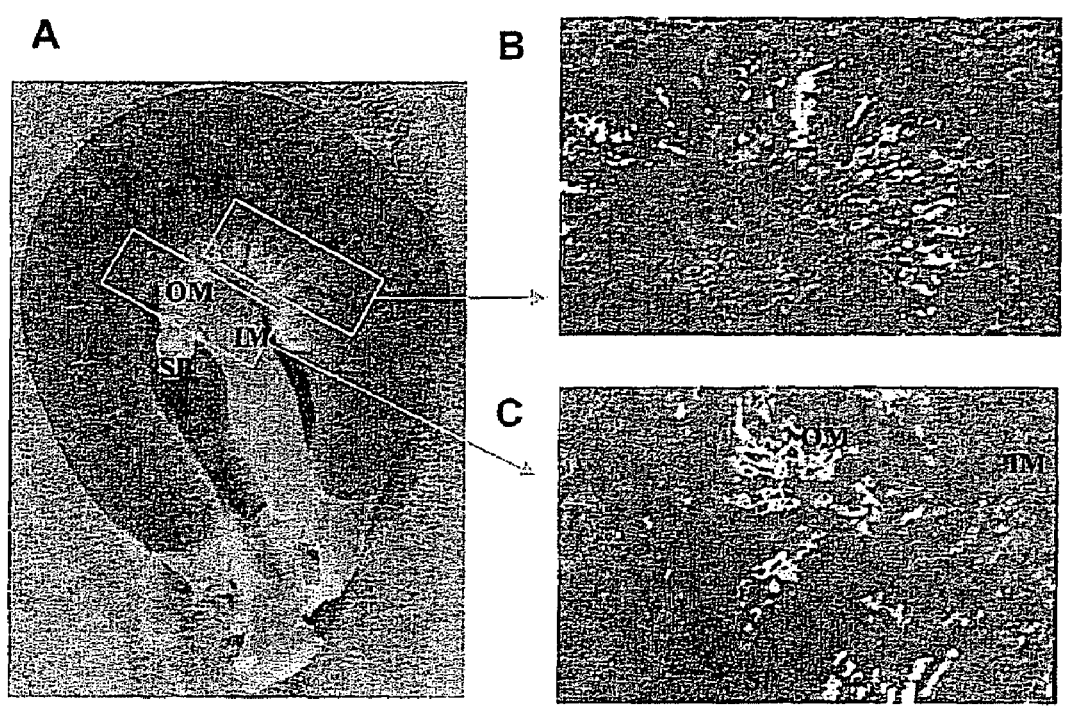
FIG. 14: Distal tubular necrosis, cell death induced by radio-contrast; detection by DDC; (A) macroscopic appearance of the renal damage; (B) area of damage marked with DDC (C) damage detected in OM (outer medulla), IM (inner medulla), and SP (secondary pyramid).
Figure 15A:
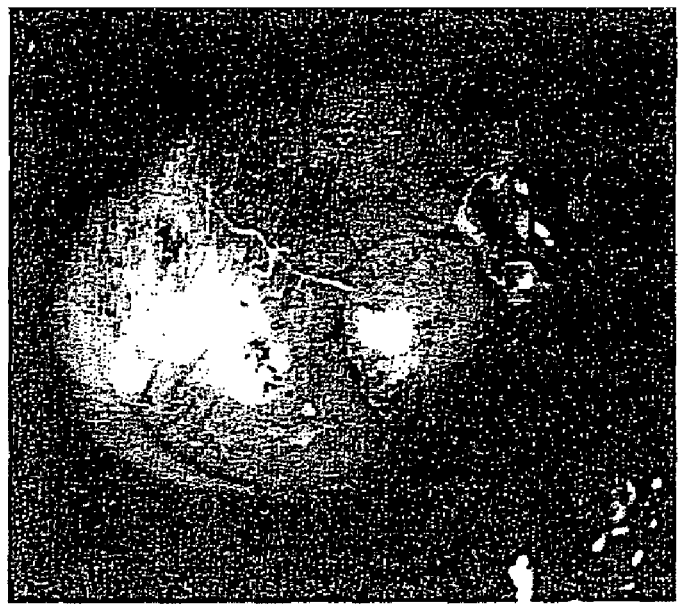
FIG. 15: Detection by DDC of ischemic damage in the mouse heart following ischemia-reperfusion (I/R); (A) upper-uptake of DDC, down-lack of uptake of DDC in a mouse with I/R treated with a caspase inhibitor; (B) uptake of DDC into single damaged cardiomyocytes; (C) cryosections prepared from the ischemic heart where uptake of DDC is demonstrated.
Figure 15A:
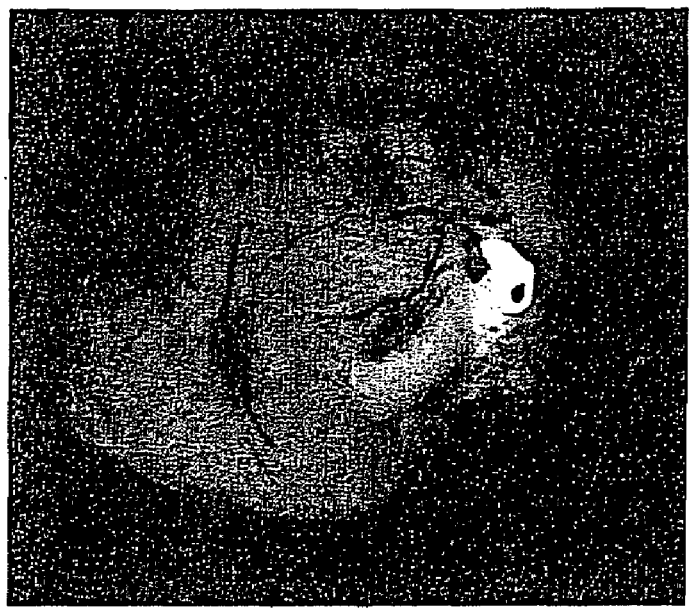
Figure 15B:
Figure 15C:
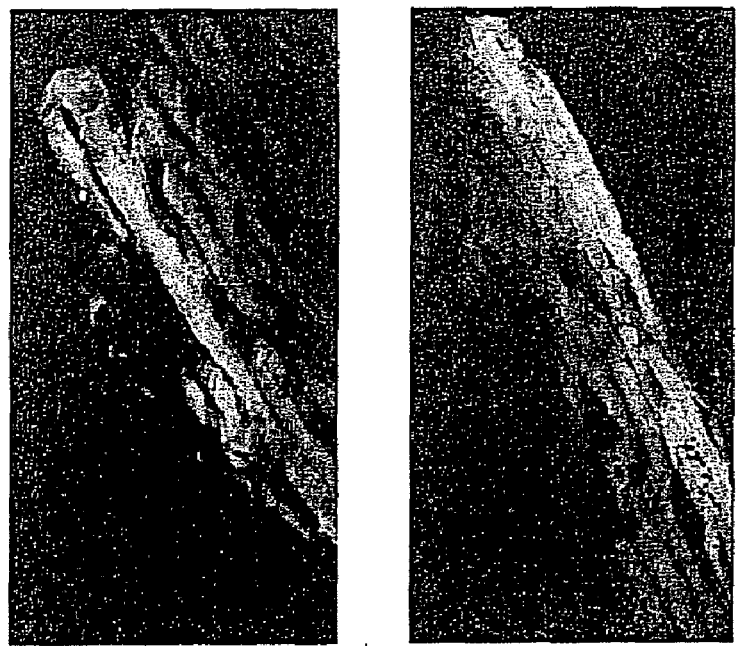
Figure 16A:
FIG. 16: Focal uptake of DDC in cells undergoing cell death in the murine heart, following sepsis caused by cecal ligature and perforation (CLP); (A-F) fluorescence of DDC in a single cardiomyocytes undergoing cell death.
Figure 16B:
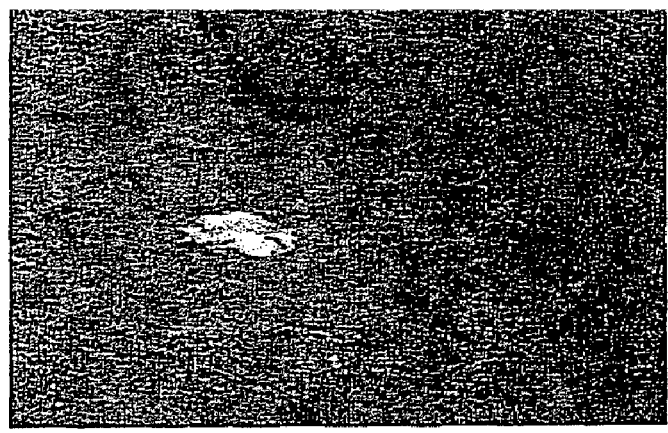
Figure 16C:
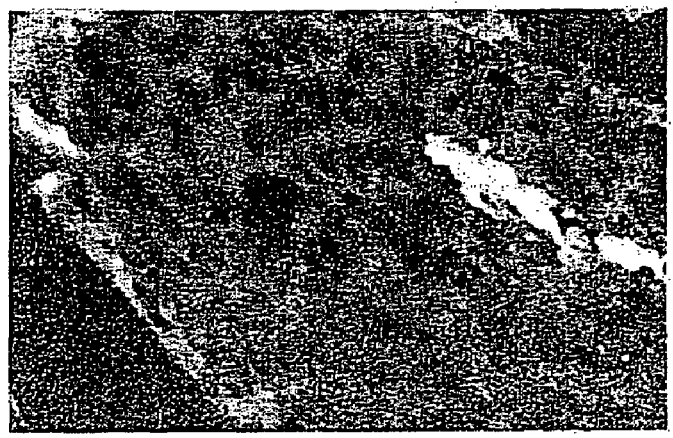
Figure 16C:
Figure 16D:
Figure 16E:
Figure 17A:
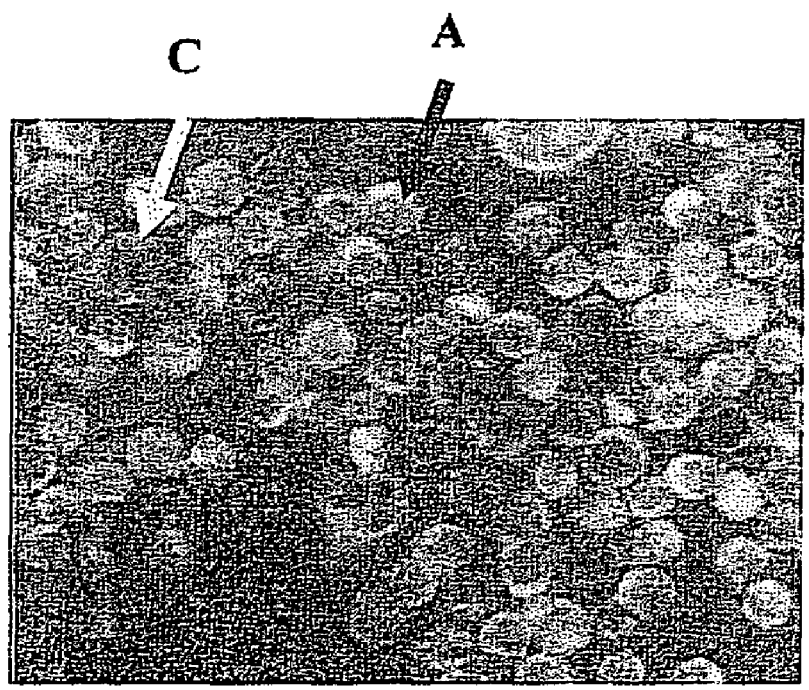
FIG. 17: Rapid binding of DDC to C26 colon carcinoma cells, undergoing cell death induced by BiCNU; (A) 40 seconds after initiation of contact with DDC; (B) 2 minutes; (C) 5 minutes and (D) 9 minutes.
Figure 17B:
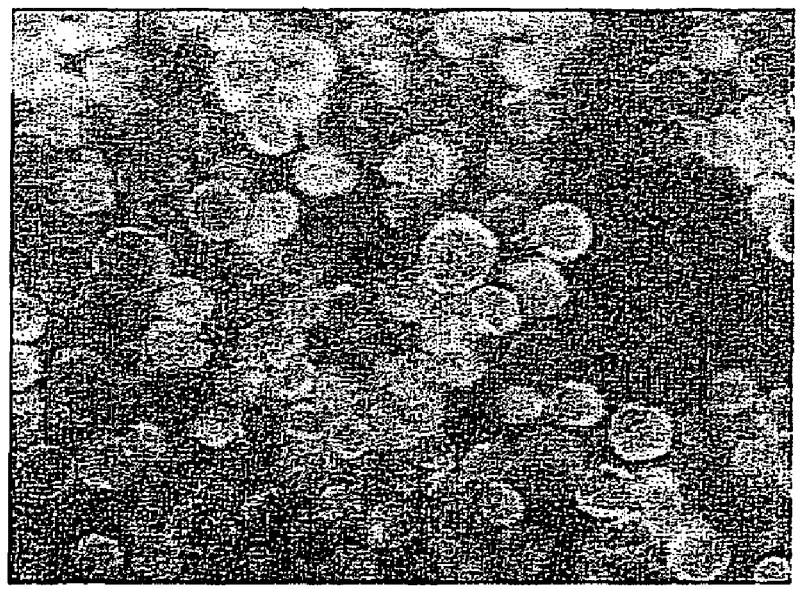
Figure 17C:
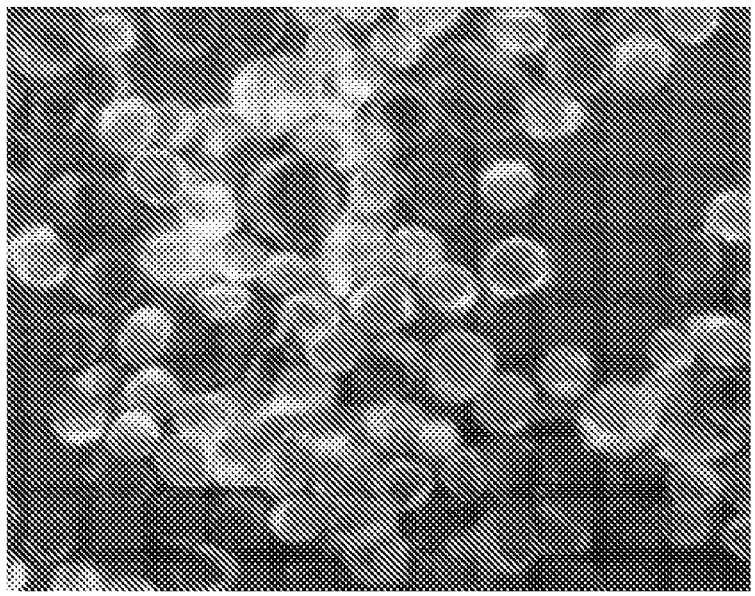
Figure 17D:
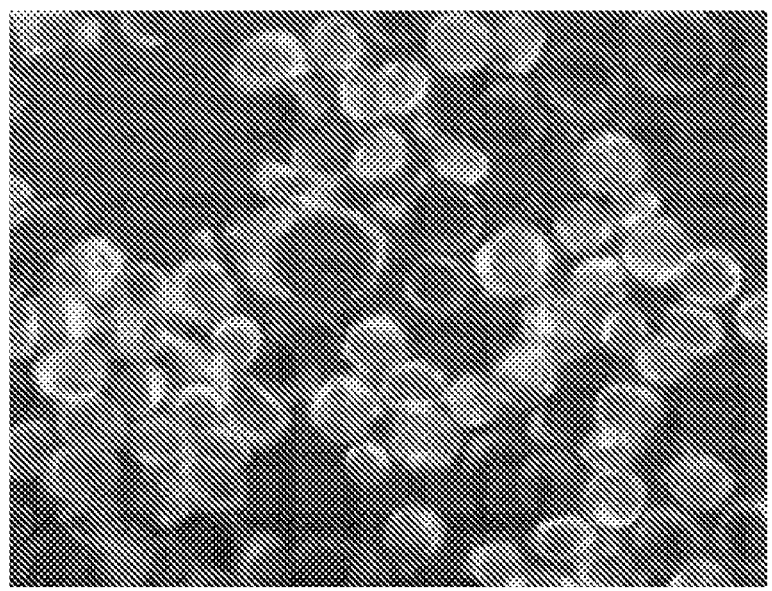

The selectivity of DDC uptake in injured renal tissues was evaluated in this rat model, characterized by selective medullary hypoxic tubular damage. Nephropathy was induced as previously described (Agmon Y, et al., 1994, Heyman S N, et al., 1977). Twenty-four hours after insult, animals were intravenously injected with DDC and 2 hours later they were sacrificed The left kidney was removed and snap-frozen for fluorescence analysis (and for H&E and TUNEL staining), whereas the right kidney, was used for morphologic evaluation, and was in vivo fixed with glutaraldehyde perfusion through the abdominal aorta. As shown in FIG. 14, DDC distribution pattern (B and C) closely followed the characteristic striped pattern of morphological findings in the contralateral perfused kidney (A). Homing of DDC was restricted to infused regions within the outer and inner stripe of the outer medulla OM-outer medulla, IM-inner medulla, SP-secondary pyramid Example 15

Detection by DDC of Ischemic Damage in the Mouse Heart Following Ischemia-reperfusion (I/R)

Ischemia/Reperfusion was induced in male Swiss mice by ligation and subsequent release of a suture around the left anterior descending coronary artery. Ischemia was for 40 minutes followed by reperfusion of 90 minutes. DDC was injected to the Jugular vein at the onset of ischemia. Uptake of DDC was followed at real time in the beating heart using a Laica stereomycroscope. Pictures were taken at the end point of the reperfusion (90 minutes) and collected by Hamamatsu CCD camera. For inhibition by caspase inhibitors, animals were injected with a pan-Caspase inhibitor in two doses of 10 mg/kg given at the time of reperfusion. As seen, the use of caspase inhibitor completely blocked DDC uptake, emphasizing its specificity for the apoptotic process, and demonstrating a possible use of following caspase inhibition in-vivo (Figure A right side in comparison to non caspase treated animal—left side). Uptake of DDC was identified in individual cadiomyocites as can be seen in FIG. 15, (B) and (C). (B) Real time images taken, while the heart was beating, of cardiomyocyts demonstrating uptake of DDC into individual cells. Figures (C) and (D) Cryosections prepared from the heart that was collected at the end point of the experiments DDC fluorescence can be viewed in single apoptotic cardiomyocites. This example support the role of DDC in detecting ischemic cells in the level of a single apoptotic cell.

Example 16

Focal Uptake of DDC in Heart of Mice Following Sepsis, Caused by Cecal Ligature and Perforation (CLP)

The cecum of anesthetized mice was isolated, ligated distal to the ileocaecal valve, and punctured twice with 26-gauge needle. Twenty-four hours later mice were injected i.v. with DDC and two hours afterwards kidneys were removed and frozen in liquid nitrogen, histological sections were prepared and subjected to analysis. The fluorescence of DDC can be seen in single cardiomyocites following the sepsis (see FIG. 16 A-F), the results suggest the role of DDC in following up damages caused by sepsis.

Example 17

Binding of DDC to Carcinoma Cells were Treated with 0.5 mM BiCNU

C26 colon carcinoma cells were treated with 0.5 mM BiCNU for 2 hr. Staining with DDC (as detailed in DDC protocol IIIC) was performed for the indicated time periods. The cell in which "A" arrow is pointed to are cells that acquired DDC, while the cells in which "C" arrow is pointed to is a live cell, presenting blue autofluoresence. Selective binding of DDC to apoptotic cells occurred very rapidly and in 40 seconds the apoptotic cells were already stained. (A) 40 seconds after contacting with DDC; (B) 2 minutes; (C) 5 minutes and (D) 9 minutes.

Example 18

Binding of DDC and PI to Jurkat Cells Treated with CD95

Jurkat cells (T-cell leukemia) were treated with CD95 for 180 minutes and incubated with DDC followed by incubation with Propidium Iodide (PI) as detailed in DDC protocols IIIC. The cells were analyzed under fluorescent confocal microscope using a UV filter. DDC accumulated within the cytoplasm of early and late apoptotic cells. Nuclear staining by PI can be seen only in late apoptotic cells. Data not shown.

Example 19

Figure 18A:
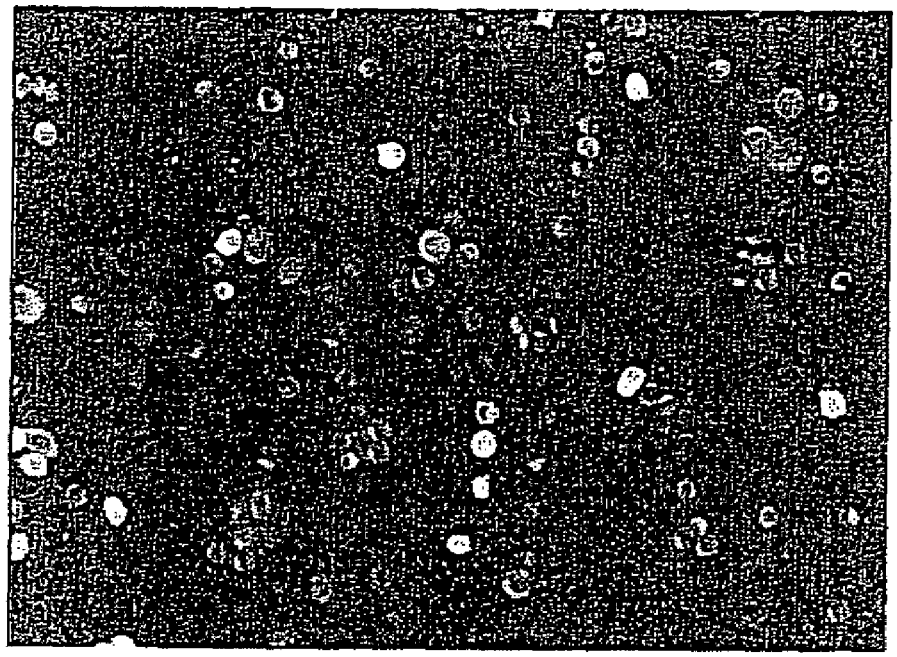
FIG. 18: Staining by DDC of C26 colon carcinoma cells undergoing cell death induced by BiCNU; (A) control; (B) cells treated with BiCNU.
Figure 18B:
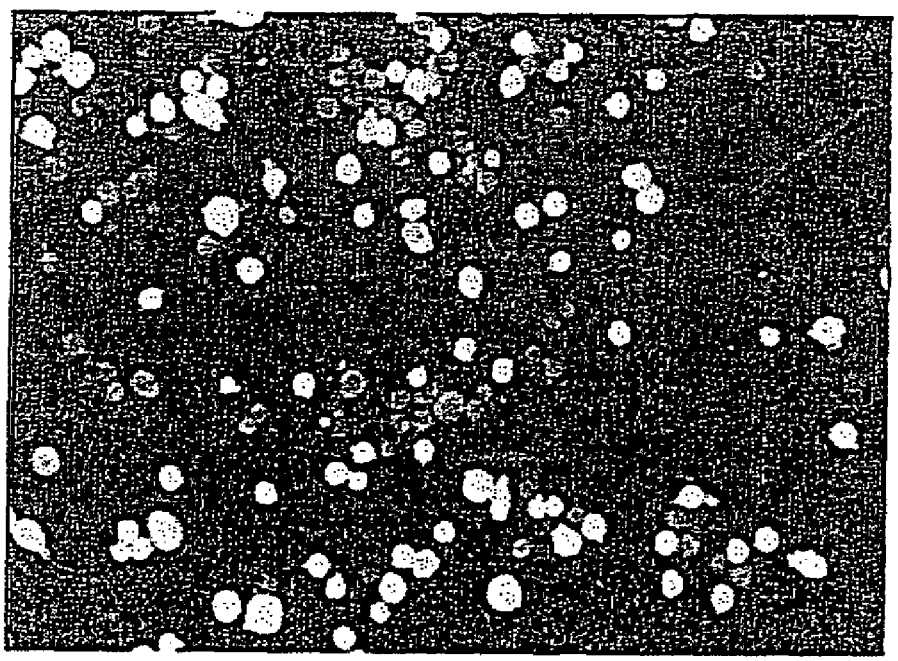

Binding of DDC to C26 Colon Carcinoma Cells Treated with 0.5 mM BiCNU 26 colon carcinoma cells were treated with 0.5 mM BiCNU for 2 hr and stained with DDC (as detailed in the DDC protocols IIIC). Cells were analyzed by fluorescent microscope under a UV filter. Control culture (FIG. 18A) contained a small percentage of stained cells reflecting the natural process of cell death occurring within the cell culture. A marked increase in the number of the stained cells can be seen following treatment with the death inducer BiCNU (FIG. 18 B).

Example 20

Binding of DDC and PI to Jurkat Cells Treated with Anti-Fas Antibody

Jurkat cells (T-cell leukemia, human) were treated with anti-Fas antibody (0.1 µg/ml) for 180 minutes, Following incubation the cells were washed and stained with DDC (as detailed in DDC protocols, IIIA). PI was added to the reaction and the cells were subjected to FACS analysis. Dot plot analysis of control and treated cells are represented in AI. Following incubation with anti-Fas antibody, most of the cells shifted to the lower right section (AII, EA) of higher fluorescence value, indicating increased staining with DDC. These cells were in the early phase of cell death and still contain an intact membrane since they do not bind the permeable PI dye. The cells in the upper right section were double stained with both PI and DDC, suggesting that DDC detected both early and late events. The population of the late apoptotic cells was small and not affected by binding to DDC. FIG. 19B presents the frequency histogram of the number of events (counts, Y axis) versus UV intensity (DDC, X-axis). A marked shift of fluorescence (DDC accumulation) can be seen in cells that were treated with anti-Fas antibody as compared to the control population. (N-normal cells, EA—Early apoptotic cells, LA—late apoptotic cells). FACS analysis using DDC alone identified three cell populations even without PI staining: control, early apoptotic and late apoptotic, each of them having a unique histogram. The difference between each cell population is characterized in Table 1, FIG. 19(C).

Example 21

Selective Binding of DDC to Activated Red Blood Cells (RBC); Flow-cytometric Analysis The selective binding of DDC to activated or damaged cells red blood cells (RBC) and to control, healthy RBC was explored and demonstrated. Activation of intact RBC, was induced by a combined treatment with N-ethylmaleimide (NEM) and calcium ionophore, in the presence of Ca 2+.

Fresh RBC were obtained, diluted to 0.1 of their initial volume with buffer A (143 mM NaCl; 2 mM KCl; 0.1% Glucose; 10 mM NaH2PO4; pH=7.4), and washed 4 times in the above buffer. Cells were then re-suspended in buffer B (55 mM NaCl; 90 mM KCl, 0.1% glucose, 10 mM HEPES; pH=7.4). These cells were thereafter used as control cells. For activation, the cells were treated for 15-60 min at 37° C. with a combination of 2 mM CaCl, 5 µM of the Calcium ionophore A23187 and 5 mm of NEM. Cells were then washed twice with buffer B containing 0.1% of bovine serum albumin, and finally re-suspended in Buffer B containing 2 mM $CaCl_2$ For examination of binding of DDC to the cells, DDC was dissolved in 0.1M NaPPi, pH=7.4, at a stock concentration of 1 mM. Binding assays were performed at a final concentration of 500 µM, and level of binding was evaluated by flow cytometry.

Figure 20:
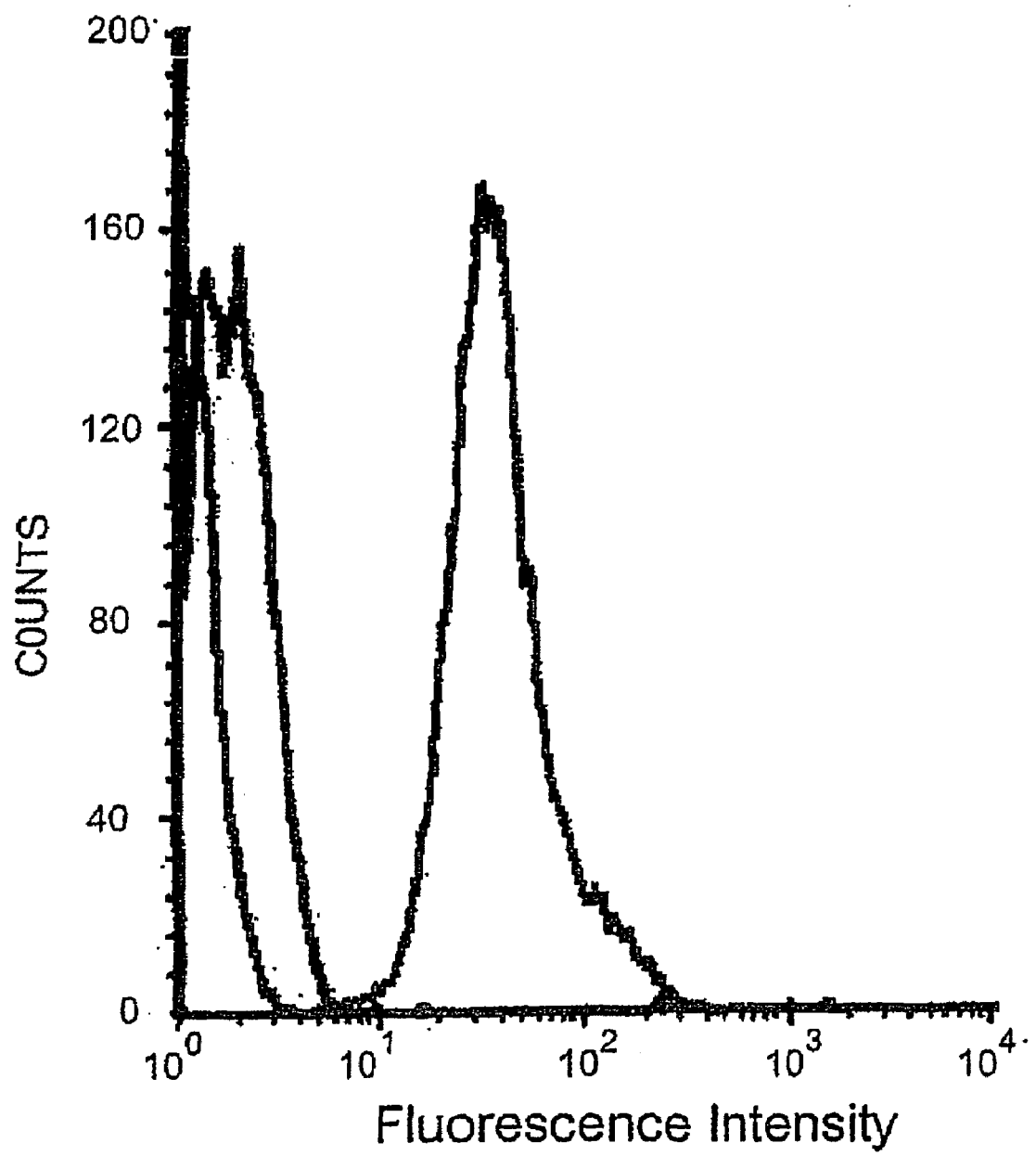
FIG. 20: Selective binding of DDC to red blood cells (RBC), activated by N-ethylmaleimide; flow-cytometric analysis.

As shown in FIG. 20, intact red blood cells did not stain significantly with DDC. However, as a result of RBC activation, the whole population of cells underwent a substantial shift to higher fluorescence levels, reflecting DDC binding. Therefore, DDC manifests selective binding to activated/damaged RBC.

Example 22

Selective Binding of DDC to Activated Platelets

The selective binding of DDC to activated platelets was determined using flow cytometric (FACS) analysis. Platelet-rich plasma was obtained from healthy volunteers. $10^9$ of the fresh platelets were centrifuged (5 minutes, 380×g), washed and re-suspended in Tyrode's buffer (137 mM NaCl; 2.8 mM KCl; 1 mM $MgCl_2$, 12 mM NaHCO3; 0.4 mM Na2HPO4; 5.5 mM D-glucose and 10 mM Hepes pH 7.4; 0.35% BSA). The purified platelets were kept on ice, and served as controls.

For activation, 200 µl of washed platelets were incubated with a mixture of 0.05 units/ml of thrombin and 5 µg/ml collagen for 5 min. at 37°, in the presence of 2 mM $CaCl_2$ in a final volume of 1 ml. Following incubation, the platelets were centrifuged (2 min. at $10^4$ rpm) and resuspended in 1 ml of Tyrode's buffer.

Figure 21A:
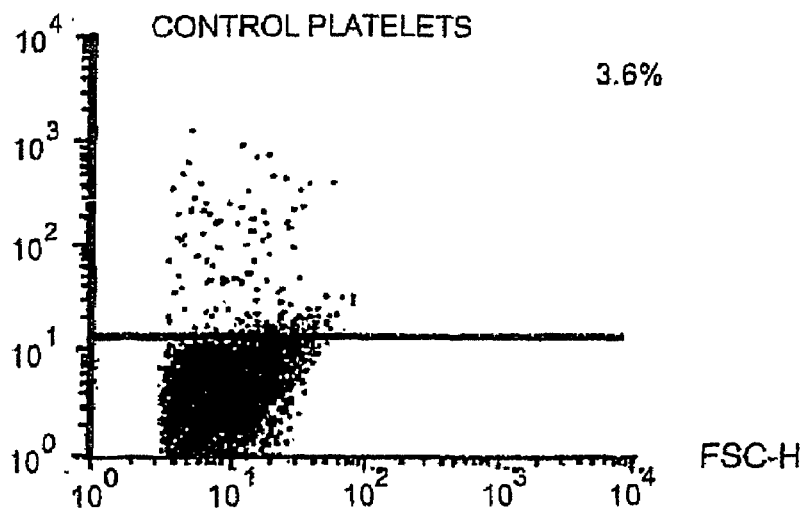
FIG. 21: Selective binding of DDC to platelets activated by thrombin and collagen; flow-cytometric analysis.
Figure 21B:
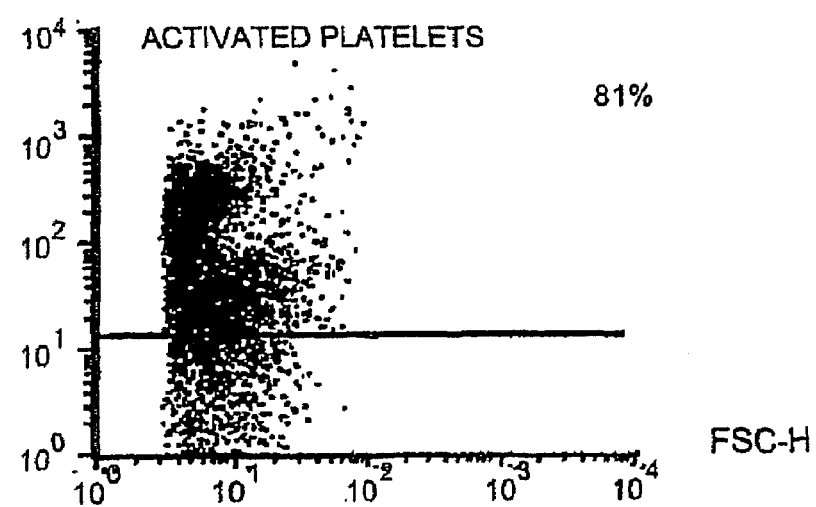
Figure 21C:
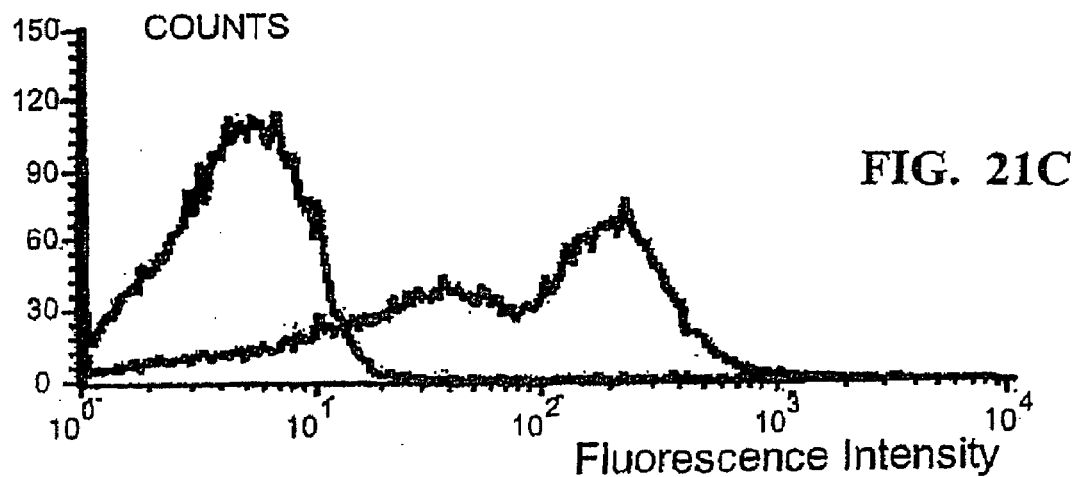
Figure 22:
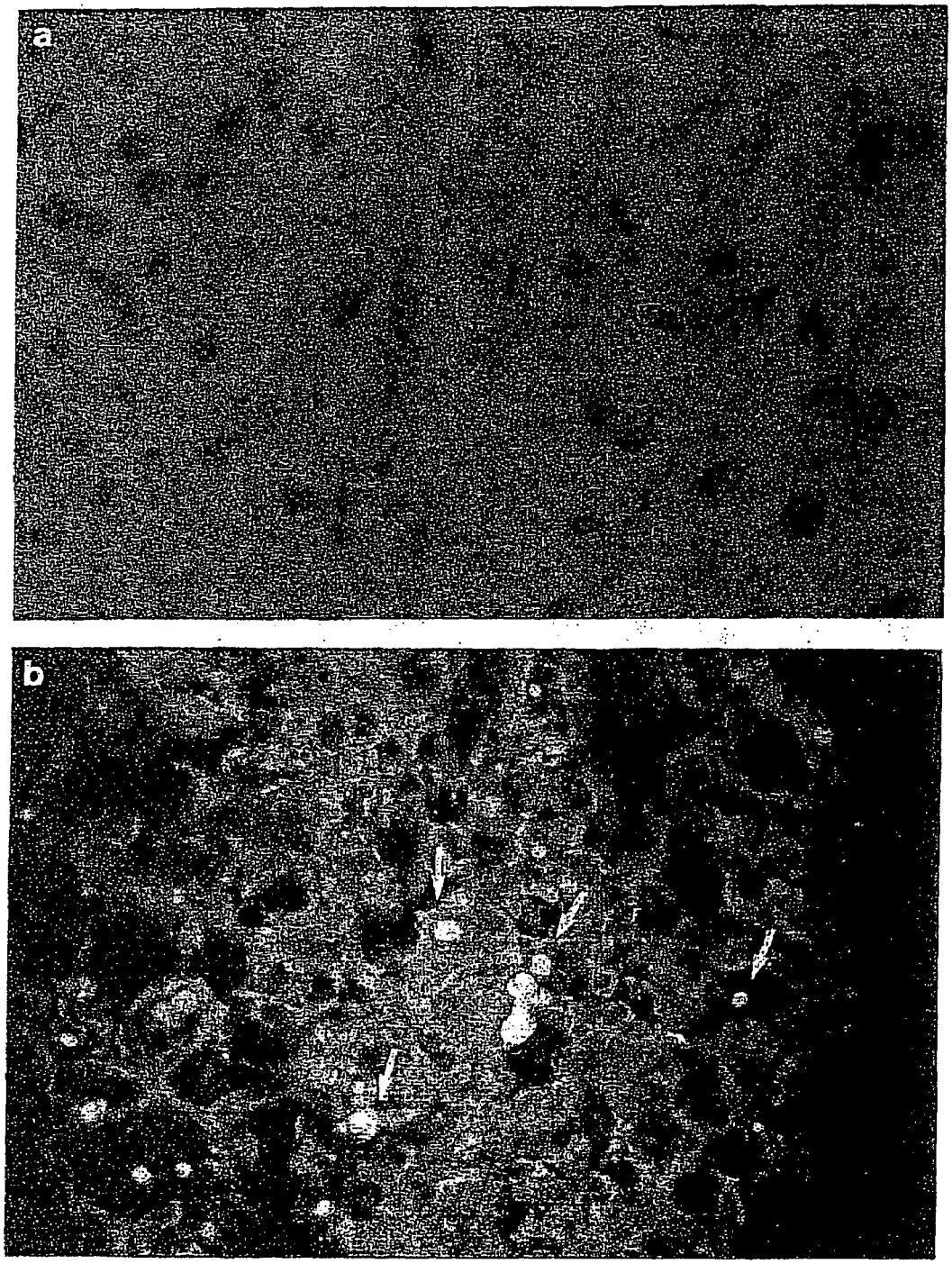
FIG. 22: Detection by DDC in vivo of liver-cell apoptosis induced by anti-Fas antibody.

Activated and control non-treated platelets were incubated with 10 µM of DDC for 5 minutes at room temperature. The platelets were then subjected to analysis by flow cytometry (FACS) using Beckton-Dickinson cell sorter and CellQuest software. Excitation was at 360 nm and emission was measured at 530 nm. FIG. 21A. Shows the fraction of platelets binding DDC upon activation. While only a small fraction of the control platelets manifested binding of DDC (3.6% of the population), platelet activation caused 81% of the platelet population to acquire a marked DDC binding, reflected as a distinct shift to higher fluorescence intensity. As shown in tile FACS histogram in FIG. 21B, activation was associated with a major shift of the whole platelet population to higher fluorescence intensity. DDC can therefore act, through its detection of PNOM, as a potent agent to mark and distinguish between activated and non-activated platelets.

Example 23

Selective Binding of DDC to Apoptotic Cells In Vivo

Selective detection of apoptotic cells in vivo has numerous diagnostic and therapeutic clinical applications. In order to demonstrate the potential of DDC in performing this task, a well-characterized model of hepatic apoptosis in vivo, induced by intravenous administration of anti-Fas antibody was utilized. Treatment of mice with anti-Fas monoclonal agonistic antibody induces apoptosis of hepatocytes, leading to animal death of within several hours. The study included intravenous administration of DDC to anti-Fas-Ab-injected mice, as well as to control, untreated animals. Fluorescence histopathological studies were then performed to evaluate the level of DDC binding.

Five-week-old male BALB/c mice were injected intravenously with 10 µg/animal of purified hamster anti-Fas nAb. Mice were then injected intravenously with 70 mg/Kg of DDC. Injections were performed 30 minutes after antibody treatment. Control animals were injected with DDC only, without antibody administration. All animals were sacrificed three hours after administration of the antibody, followed by organ removal. Liver was sectioned transversely across the mid-portion of each lobe, dipped immediately into liquid nitrogen, and then transferred to −80° C. for 24 hours. Organs were then transferred into OCT solution, and cryosections (5 µm) were prepared. These sections were taken for fluorescent microscopy. Parallel sections were stained with hematoxylin/eosin (H&E), for simultaneous evaluation of the characteristic apoptotic morphology of the cells manifesting DDC binding.

Control animals, injected with DDC did not manifest significant fluorescence in the liver sections, i.e., no significant binding of DDC was observed (FIG. 21A). By contrast, marked, specific binding of DDC to numerous apoptotic cells was observed in the livers from animals treated with the anti-Fas Ab (FIG. 21B; arrows mark several of the apoptotic cells). Comparison with the H&E staining confirmed the indeed the cells which manifested DDC binding had characteristic apoptotic morphology.

These experiments therefore demonstrate the potential of DDC, upon systemic administration, to detect and selectively bind to apoptotic cells in vivo Example 24

Detection of Apoptotic Cells in Vivo within a Tumor by DDC

One of the characteristics of primary tumors is the occurrence of tumor cell apoptosis, in parallel to the proliferation of the neoplastic cells. It is clear now, that the net balance between proliferation and apoptosis within a primary tumor is an important prognostic factor and a predictor of metastases. A high prevalence of apoptotic cells is associated with a more malignant tumor and poorer prognosis. Therefore, a non-invasive diagnostic and predictive tool to evaluate the apoptotic load within a tumor in-vivo has potential important applications in clinical oncology.

DDC was therefore used to detect apoptotic cells within tumors. Primary tumors of Lewis Lung carcinoma (3LL) were induced in 12 weeks old c57 black mice by subcutaneous injection of $0.5 \times 10^6$ cells/animal of D122 tumor cells. Tumor cell line was maintained as described by Eisenbach L, et al., (*Int. J. Cancer,* 34:567-573, 1984). Two weeks following the injection, when tumors of 2-3 mm were observed, animals were injected intravenously with 70 mg/kg of DDC. Tumor was removed two hours later, and quickly frozen in liquid nitrogen Cryo-sections were then prepared and subjected to histopathological analysis, using a fluorescent microscope (magnification ×600).

Figure 23:
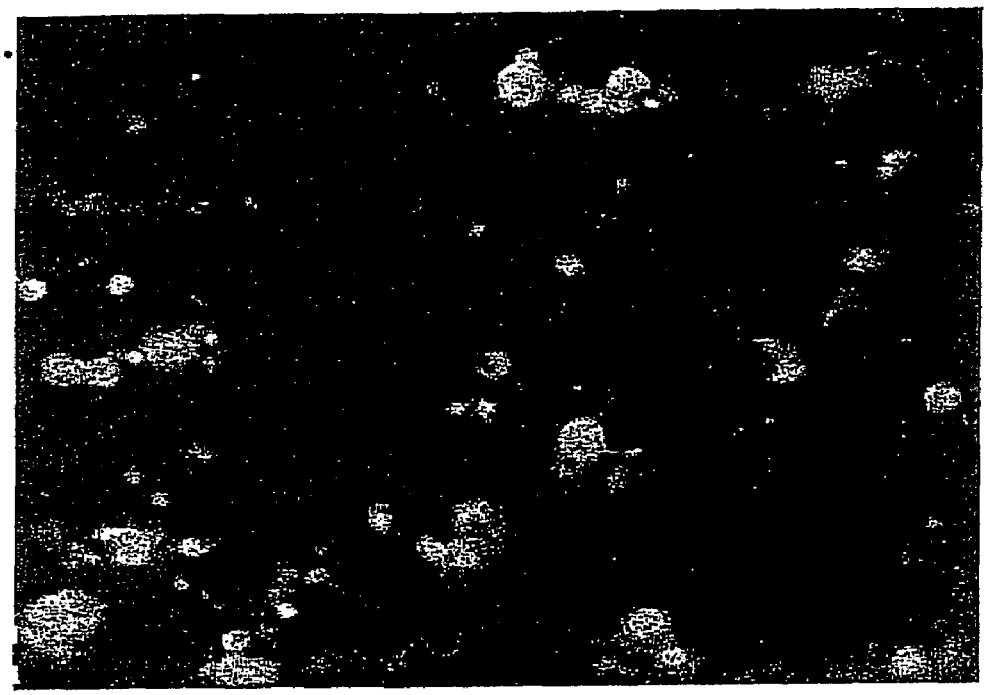
FIG. 23: Detection by DDC in vivo of apoptotic cells within a tumor, correlation with TUNEL ex-vivo assay.
Figure 23:

The ability of DDC to detect apoptotic cells within the tumor upon systemic administration in-vivo, is demonstrated in FIG. 23A. Such detection allows for calculation of the apoptotic index (AI) of the tumor. In order to demonstrate that this index, achieved with the DDC does indeed reflect the apoptotic load within the tumor, a parallel staining with TUNEL, a well-accepted method for detection of the characteristic apoptotic internucleosomal DNA cleavage was used (FIG. 23B). Similar number of apoptotic cells can be observed within the tumor, using both detection methods. DDC is therefore capable of detecting the apoptotic load within a tumor in vivo. Its sensitivity in measuring the AI of the tumor in vivo, upon systemic intravenous administration, is similar to the direct characterization achieved by the TUNEL procedure on tissue sections ex-vivo.

What is claimed is:

1. A method of detecting PNOM-cells within a population of cells, comprising the steps of:
   (i) contacting the cell population with a PMBC, wherein said PMBC is according to the structure set forth in formula I;

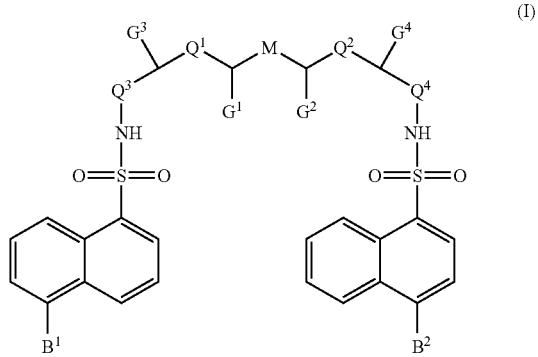

wherein $G^1$, $G^2$, $G^3$ and $G^4$ groups may be the same or different and are selected independently among hydrogen, COOH, $SO_3H$ and $PO_3H$; at least one of G groups is other than hydrogen;

M is selected among null, O, S, and S—S;

$Q^1$, $Q^2$, $Q^3$ and $Q^4$ groups may be the same or different and are selected among null or $(CH_2)_k$, k being an integer of 1-4;

$B^1$ and $B^2$ may be same or different, selected from hydrogen, $R^6$—N—$R^7$, OH and —O—$R^6$;

wherein $R^6$ or $R^7$ may be same or different, each being selected from hydrogen and $C_1$, $C_2$, $C_3$ or $C_4$ linear or branched, substituted or un-substituted alkyl; and (ii) determining the amount of PMBC bound to cells in the cell population; wherein an amount of PMBC bound to cells, which is significantly higher than the amount bound to control cells, indicates the presence of PNOM-cells within the examined cell population.

2. A method according to claim 1, for the detection of cells undergoing a death process.

3. The method of claim 1, wherein the compound is according to the structure set forth in formula II:

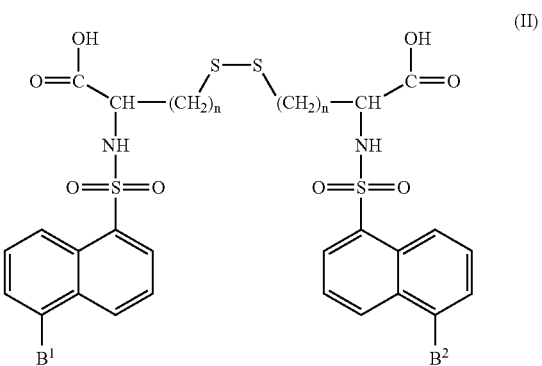

wherein $B^1$ and $B^2$ may be same or different, selected from hydrogen, $R^6$—N—$R^7$, OH and —O—$R^6$;

wherein $R^6$ or $R^7$ may be same or different, each being selected from hydrogen and $C_1$, $C_2$, $C_3$ or $C_4$ linear or branched, substituted or un-substituted alkyl; and wherein n stands for an integer of 1-3.

4. The method of claim 1, wherein the compound is according to the structure set forth in formula III:

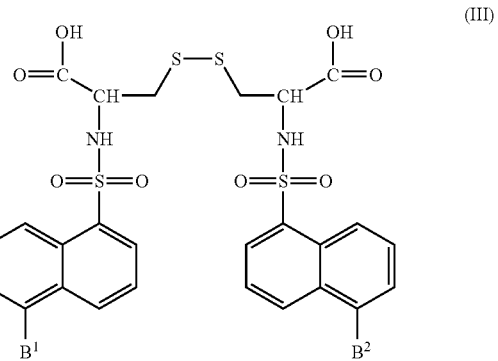

wherein $B^1$ and $B^2$ may be same or different, selected from hydrogen, $R^6$—N—$R^7$, OH and —O—$R^6$; wherein $R^6$ or $R^7$ may be same or different, each being selected from hydrogen and $C_1$, $C_2$, $C_3$ or $C_4$ linear or branched substituted or un-substituted alkyl.

5. The method of claim 1, wherein the compound is according to the structure set forth in formula IV:

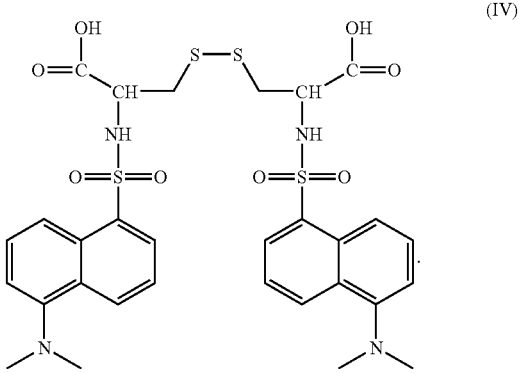

6. The method of claim 1, wherein the cell population is a tumor and said detection enables monitoring the aggressiveness of a tumor, or response of a tumor to an anti-cancer treatment, wherein said anti-cancer treatment induces a cell death process or apoptosis.

7. The method of claim 1 wherein said step of determining the amount of PMBC bound to cells in said cell population is by measuring she fluorescence.

8. A method for detecting the presence of PNOM-cells in a tissue of an animal, in-vivo or ex-vivo comprising the steps of:
(i) administering a PMBC to the animal, wherein said PMBC is according to the structure set forth in formula I;

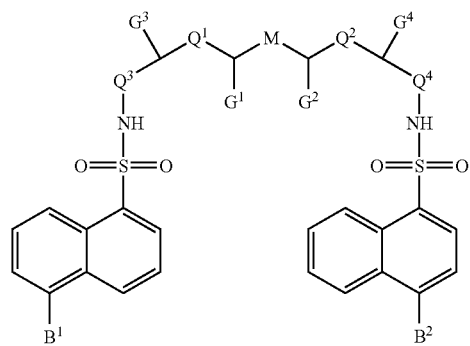

(I)

wherein $G^1$, $G^2$, $G^3$ and $G^4$ groups may be the same or different and are selected independently among hydrogen, COOH, $SO_3H$ and $PO_2H$; at least one of G groups is other than hydrogen;

M is selected among null, O, S, and S—S;

$Q^1$, $Q^2$, $Q^3$ and $Q^4$ groups may be the same or different and are selected among null or $(CH_2)_k$, k being an integer of 1-4;

$B^1$ and $B^2$ may be same or different, selected from hydrogen, $R^6$—N—$R^7$, OH and —O—$R^6$;

wherein $R^6$ or $R^7$ may be same or different each being selected from hydrogen and $C_1$, $C_2$, $C_3$ or $C_4$ linear or branched, substituted or un-substituted alkyl; and (ii) determining the amount of PMBC bound to cells in said tissue;

wherein an amount of compound bound to cells in a tissue, which is significantly higher than the amount of compound bound to cells in a control tissue indicates that the tissue contains PNOM-cells.

9. A method according to claim 8, for the detection of cells undergoing a death process.

10. The method of claim 8, wherein the compound is according to the structure set forth in formula II:

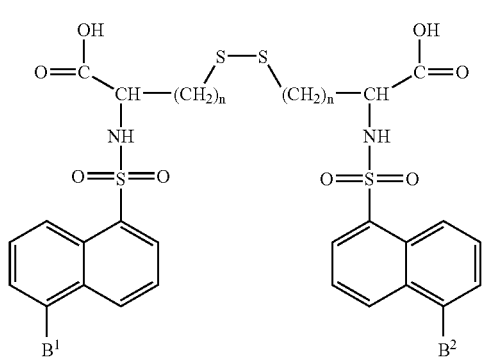

(II)

wherein $B^1$ and $B^2$ may be same or different, selected from hydrogen, $R^6$—N—$R^7$, OH and —O—$R^6$;

wherein $R^6$ or $R^7$ may be same or different each being selected from hydrogen and $C_1$, $C_2$, $C_3$ or $C_4$ linear or branched, substituted or un-substituted alkyl; and wherein n stands for an integer of 1-3.

11. The method of claim 2, wherein the compound is according to the structure set forth in formula III:

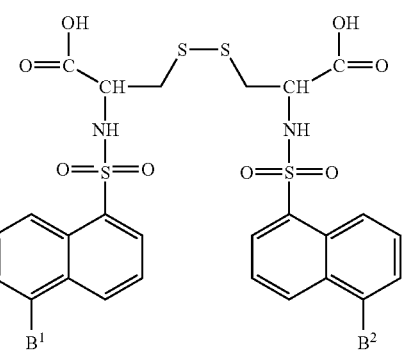

(III)

wherein $B^1$ and $B^2$ may be same or different, selected from hydrogen, $R^6$—N—$R^7$, OH and —O—$R^6$; wherein $R^6$ or $R^7$ may be same or different, each being selected from hydrogen and $C_1$, $C_2$, $C_3$ or $C_4$ linear or branched, substituted or un-substituted alkyl.

12. The method of claim 2, wherein the compound is according to the structure set forth in formula IV:

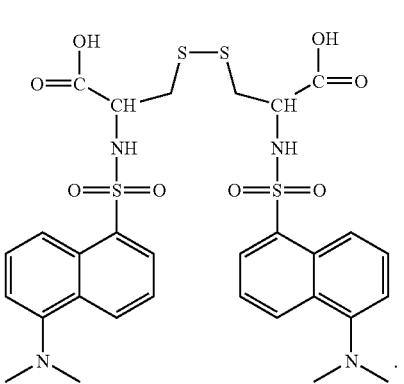

(IV)

13. The method of claim 2, wherein the cell population is a tumor said detection enables monitoring the aggressiveness of a tumor, the response of a tumor to anti-cancer treatment, or monitoring of adverse effects of anti-cancer treatment wherein said anti-cancer treatment induces a cell death process or apoptosis.

14. The method of claim 2, determining the amount of PMBC bound to cells in said tissue is by measuring the fluorescence.

* * * * *